US012360095B2

United States Patent
Nakao

(10) Patent No.: US 12,360,095 B2
(45) Date of Patent: Jul. 15, 2025

(54) GAS DETECTION SYSTEM AND CONTROL METHOD FOR GAS DETECTION SYSTEM

(71) Applicant: Panasonic Intellectual Property Management Co., Ltd., Osaka (JP)

(72) Inventor: Atsuo Nakao, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 323 days.

(21) Appl. No.: 17/801,174

(22) PCT Filed: Feb. 26, 2021

(86) PCT No.: PCT/JP2021/007298
§ 371 (c)(1),
(2) Date: Aug. 19, 2022

(87) PCT Pub. No.: WO2021/172504
PCT Pub. Date: Sep. 2, 2021

(65) Prior Publication Data
US 2023/0063005 A1    Mar. 2, 2023

(30) Foreign Application Priority Data

Feb. 27, 2020 (JP) ................................. 2020-032384
Feb. 27, 2020 (JP) ................................. 2020-032385
(Continued)

(51) Int. Cl.
| | | |
|---|---|---|
| G01N 33/00 | (2006.01) | |
| G01N 1/34 | (2006.01) | |
| G01N 27/12 | (2006.01) | |

(52) U.S. Cl.
CPC ............. *G01N 33/007* (2013.01); *G01N 1/34* (2013.01); *G01N 27/121* (2013.01); *G01N 33/0072* (2024.05)

(58) Field of Classification Search
CPC ...... G01N 1/34; G01N 27/121; G01N 33/007; G01N 33/0072; G01N 5/02; G01N 1/2205;
(Continued)

(56) References Cited

U.S. PATENT DOCUMENTS

| | | |
|---|---|---|
| 6,165,336 A | 12/2000 | Maki et al. |
| 2005/0252273 A1 | 11/2005 | Imoto |

(Continued)

FOREIGN PATENT DOCUMENTS

| | | |
|---|---|---|
| JP | H05-072094 A | 3/1993 |
| JP | H09-096622 A | 4/1997 |

(Continued)

OTHER PUBLICATIONS

International Search Report dated May 11, 2021 issued in International Patent Application No. PCT/JP2021/007298, with English translation.

*Primary Examiner* — John E Breene
*Assistant Examiner* — Truong D Phan
(74) *Attorney, Agent, or Firm* — Rimon P.C.

(57) ABSTRACT

A gas detection system includes a gas sensor, and a filter unit. The gas sensor is configured to detect detection target molecules. The filter unit is disposed at a reference gas supply passage. The reference gas supply passage connects a reference gas inlet port from which a reference gas is introduced, and a sensor chamber in which the gas sensor is housed. The filter unit includes at least a first filter configured to reduce the detection target molecules in the reference gas, and a second filter configured to reduce moisture in the reference gas. Each of the first filter and the second filter has a separation membrane including hollow fibers.

19 Claims, 10 Drawing Sheets

(30) Foreign Application Priority Data

Feb. 27, 2020 (JP) .................................. 2020-032386
Feb. 27, 2020 (JP) .................................. 2020-032387

(58) Field of Classification Search
CPC ... G01N 2001/2288; G01N 2021/3166; G01N 2021/3177; G01N 2021/8571; G01N 2035/00475; G01N 2035/1053; G01N 2201/0235; G01N 2223/651; G01N 2223/652; C12N 15/1003

USPC .......................................... 73/863.23, 31.02
See application file for complete search history.

(56) References Cited

U.S. PATENT DOCUMENTS

2007/0261559 A1    11/2007   Maroulis et al.
2012/0174925 A1*   7/2012   Tham .................. A61M 16/024
                                                   128/205.12

FOREIGN PATENT DOCUMENTS

| | | | |
|---|---|---|---|
| JP | 09304244 A | * | 11/1997 |
| JP | H09-304244 A | | 11/1997 |
| JP | 11126113 A | * | 5/1999 |
| JP | H11-126113 A | | 5/1999 |
| JP | 11281613 A | * | 10/1999 |
| JP | H11-281605 A | | 10/1999 |
| JP | 2002-090270 A | | 3/2002 |
| JP | 2004-053582 A | | 2/2004 |
| JP | 2007-318122 A | | 12/2007 |
| WO | 97/13147 A1 | | 4/1997 |

* cited by examiner

FIG. 8

GAS DETECTION SYSTEM AND CONTROL METHOD FOR GAS DETECTION SYSTEM

CROSS-REFERENCE OF RELATED APPLICATIONS

This application is the U.S. National Phase under 35 U.S.C. § 371 of International Patent Application No. PCT/JP2021/007298, filed on Feb. 26, 2021, which in turn claims the benefit of Japanese Patent Application No. 2020-032384, filed on Feb. 27, 2020, Japanese Patent Application No. 2020-032385, filed on Feb. 27, 2020, Japanese Patent Application No. 2020-032386, filed on Feb. 27, 2020, Japanese Patent Application No. 2020-032387, filed on Feb. 27, 2020, the entire disclosures of which Applications are incorporated by reference herein.

TECHNICAL FIELD

The present disclosure generally relates to gas detection systems, and control methods for gas detection systems, and more particularly relates to a gas detection system configured to detect detection target molecules in a sample gas, and a control method for a gas detection system.

BACKGROUND ART

Patent Literature 1 discloses a gas detection device (gas detection system) configured to alternately introduce a reference gas and an inspection gas (sample gas) into a sensor disposed in a housing to detect a specific component (detection target molecules) in the inspection gas. In Patent Literature 1, the inspection gas is caused to pass through a purifying means (filter unit) to purify the inspection gas, thereby the reference gas being generated, and then the reference gas generated is supplied to the sensor.

In the gas detection system mentioned above, the purifying means deodorizes or dehydrates the inspection gas. However, the deodorization capacity or the dehydration capacity of the purifying means may be reduced due to that the gas detection system is used over a long period, which may generate variation in the concentration of the specific component in the reference gas.

CITATION LIST

Patent Literature

Patent Literature 1: JP 2004-53582 A

SUMMARY OF INVENTION

It is therefore an object of the present disclosure to provide a gas detection system, and a control method for a gas detection system, which can realize suppressing deterioration of a filter unit.

A gas detection system according to an aspect of the present disclosure includes a reference gas inlet port, a gas sensor, and a filter unit. A reference gas is introduced from the reference gas inlet port. The reference gas is used as a reference to concentration of detection target molecules in a sample gas. The gas sensor is configured to detect the detection target molecules. The filter unit is disposed at a reference gas supply passage. The reference gas supply passage connects the reference gas inlet port and a sensor chamber in which the gas sensor is housed. The filter unit includes at least a first filter and a second filter. The first filter is configured to reduce the detection target molecules in the reference gas. The second filter is configured to reduce moisture in the reference gas. Each of the first filter and the second filter has a separation membrane including hollow fibers.

A control method for a gas detection system, according to an aspect of the present disclosure, includes a reference gas supply processing. The reference gas supply processing includes supplying a reference gas to a sensor chamber, in which a gas sensor is housed, through a filter unit. The reference gas is used as a reference to concentration of detection target molecules in a sample gas. The filter unit includes at least a first filter and a second filter. The first filter is configured to reduce the detection target molecules in the reference gas. The second filter is configured to reduce moisture in the reference gas. Each of the first filter and the second filter has a separation membrane including hollow fibers.

BRIEF DESCRIPTION OF DRAWINGS

FIG. 8 is a schematic system configuration diagram showing a fifth variation of the gas detection system;

DESCRIPTION OF EMBODIMENTS

Embodiment (1) Overview

The drawings to be referred to in the following description of embodiments are all schematic representations. That is to say, the ratio of the dimensions including thicknesses, of respective constituent elements illustrated on the drawings does not always reflect their actual dimensional ratio.

Figure 1:
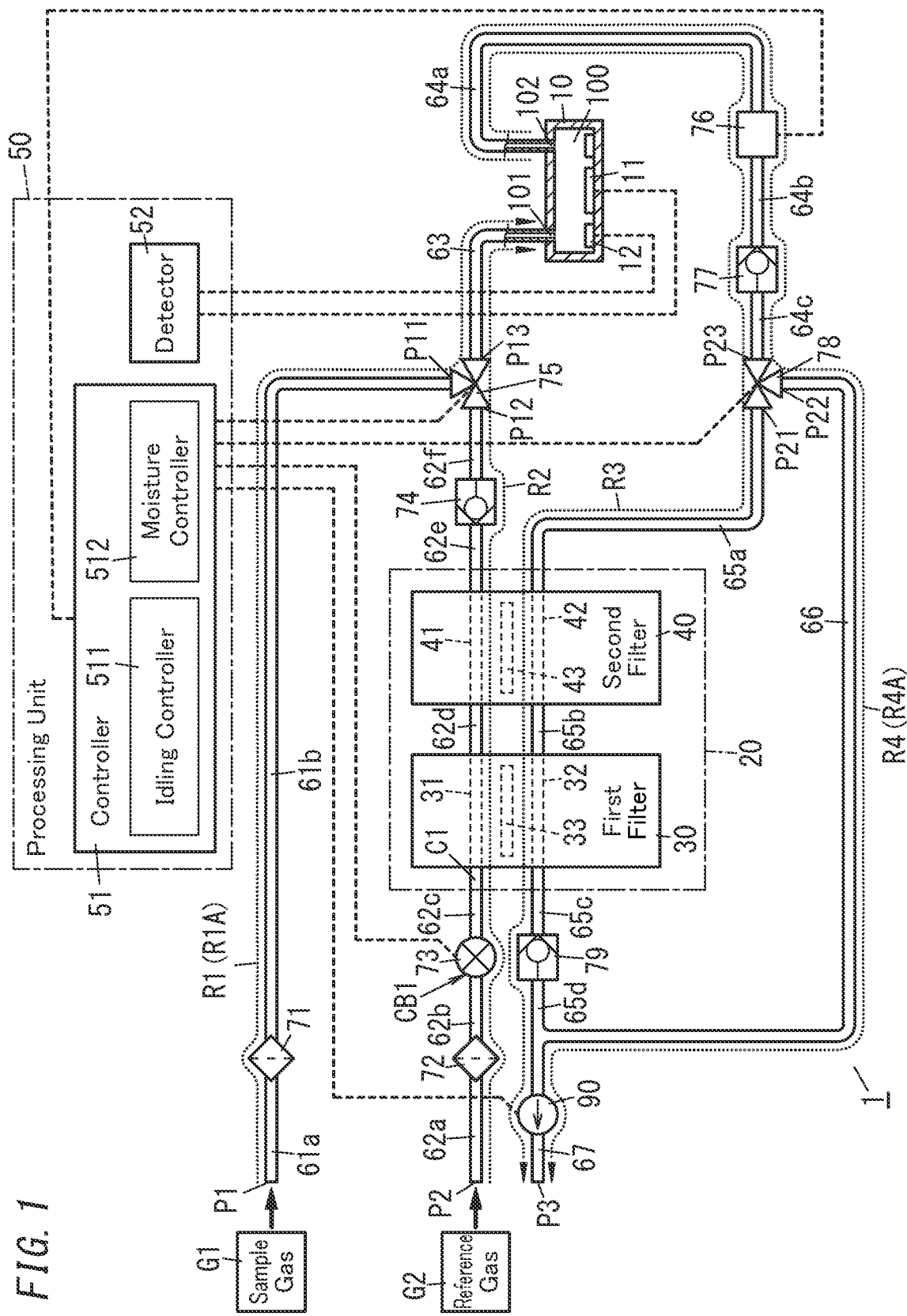
FIG. 1 is a schematic system configuration diagram of a gas detection system according to an exemplary embodiment of the present disclosure.

FIG. 1 is a schematic system configuration diagram of a gas detection system 1 according to the present embodiment.

The gas detection system 1 of the present embodiment is applied to detect, as detection target molecules, odor component molecules, for example. Examples of the odor component molecules include volatile organic compounds (VOC), and ammonia. The gas detection system 1 of the present embodiment is applied to detect, as the detection target molecules, the VOC. The gas detection system 1 of the present embodiment is configured to detect the VOC, which is the odor component molecules contained in a sample gas, such as gas collected from food, exhaled breath collected from a human body, or air collected from a room in a building. The detection target molecules for the gas detection system 1 is not limited to the VOC, but may be two or more kinds of odor component molecules including the VOC, molecules other than odor component molecules (e.g., poisonous gas molecules, such as flammable gas or carbon monoxide).

The gas detection system 1 of the present embodiment includes a reference gas inlet port (a second intake port P2), a gas sensor 11, and a filter unit 20. A reference gas G2 is introduced from the reference gas inlet port. The reference gas G2 is used as a reference to concentration of detection target molecules in a sample gas G1. The gas sensor 11 is configured to detect the detection target molecules. The filter unit 20 is disposed at a reference gas supply passage R2. The reference gas supply passage R2 connects the reference gas inlet port and a sensor chamber 100 in which the gas sensor 11 is housed. The filter unit 20 includes at least a first filter 30 and a second filter 40. The first filter 30 is configured to reduce the detection target molecules (e.g., the VOC) in the reference gas G2. The second filter 40 is configured to reduce moisture in the reference gas G2. The first filter 30 and the second filter 40 respectively have separation membranes 33, 43, each of which includes hollow fibers.

A control method for the gas detection system 1, of the present embodiment, includes a reference gas supply processing. The reference gas supply processing includes supplying the reference gas G2 to the sensor chamber 100, in which the gas sensor 11 is housed, through the filter unit 20. The reference gas 2 is used as a reference to concentration of detection target molecules in the sample gas G1.

If a filter made of a filter material such as activated carbon is connected to the reference gas supply passage R2 and used over a long period, the filter performance may be reduced by filter elements adsorbing the odor component molecules over the long period. On the other hand, the first filter 30 and the second filter 40 of the present embodiment respectively have the separation membranes 33, 43, each of which includes the hollow fibers, which can realize suppressing deterioration of the filter unit 20.

The gas detection system 1 of the present embodiment preferably further includes a shutoff unit CB1 in addition to the reference gas inlet port (the second intake port P2), the gas sensor 11, and the filter unit 20. The shutoff unit CB1 is configured to shut off outside air toward the filter unit 20 in a stop state where detection operation of the gas sensor 11 is stopped.

Also, the control method for the gas detection system 1 of the present embodiment preferably further includes a shutoff processing. The shutoff processing includes shutting off the outside air toward the filter unit 20 in the stop state where the detection operation of the gas sensor 11 is stopped.

According to the gas detection system 1 of the present embodiment, the shutoff unit CB1 shuts off the outside air toward the filter unit 20 in the stop state, which can reduce a chance that the filter unit 20 is exposed to the outside air. The deterioration of the filter unit 20 can be therefore suppressed. Accordingly, the quality of the reference gas G2 becomes stabilized after the reference gas G2 passes through the filter unit 20 in the gas detection system 1 of the present embodiment, which can realize reducing variation in detection results relating to the sample gas G1.

(2) Details

Hereinafter, the gas detection system 1 and the control method therefor according to the present embodiment will be described in more detail with reference to the drawings.

(2.1) Configuration

The gas detection system 1 of the present embodiment includes the reference gas inlet port (the second intake port P2), the gas sensor 11, and the filter unit 20, as described above. The gas detection system 1 further includes a moisture measuring unit 12, a controller 51 and the shutoff unit CB1.

The gas detection system 1 further includes: a first intake port P1 from which the sample gas G1 is introduced from the outside of the gas detection system 1; the second intake port P2 (the reference gas inlet port mentioned above) from which the reference gas G2 is introduced from the outside of the gas detection system 1; and a gas outlet port P3 from which gas inside of the gas detection system 1 is discharged to the outside. In the present embodiment, air in the ambient environment of the gas detection system 1 is used as the reference gas G2.

The gas detection system 1 further includes an air pump 90. The air pump 90 sucks the sample gas G1 from the first intake port P1, or the reference gas G2 from the second intake port P2, and accordingly, the gas sucked from the first intake port P1 or the second intake port P2 is supplied to the gas sensor 11, and then discharged from the gas outlet port P3 to the outside.

The gas detection system 1 further includes a processing unit 50. The processing unit 50 includes a microcontroller, for example. The processing unit 50 has at least functions of the controller 51 mentioned above and a detector 52. The gas detection system 1 further includes two or more electromagnetic valves (for example, a two-way electromagnetic valve 73, three-way electromagnetic valves 75, 78, an electromagnetic proportional control valve 76 and so on). The controller 51 controls operations of the two or more electromagnetic valves and the air pump 90. The controller 51 further has functions of an idling controller 511 and a moisture controller 512. The idling controller 511 controls the gas detection system 1 to switch the shutoff unit CB1 to a non-shutoff state and perform idling operation to supply the reference gas G2 to the gas sensor 11 in the stop state where the detection operation of the gas sensor 11 is stopped. The moisture controller 512 causes the gas detection system 1 to execute a moisture adjustment processing that includes adjusting the amount of moisture in the reference gas G2 to be supplied to the gas sensor 11 through the filter unit 20 based on a measuring result of the moisture measuring unit 12. The detector 52 detects the detection target molecules (the VOC in the present embodiment) in gas based on an output value of the gas sensor 11 and detects the amount of moisture in gas based on an output value of the moisture measuring unit 12.

The gas detection system 1 further includes a housing 10 having a sensor chamber 100 in which the gas sensor 11 and the moisture measuring unit 12 are housed.

The gas sensor 11 has a sensing unit, which is for example an electrochemical type, a semiconductor type, a field effect transistor type, a surface acoustic wave type, a crystal vibration type, or a variable resistance type. The sensing unit has the sensitivity to the detection target molecules (the VOC in the present embodiment), and, for example, the resistance value of the sensing unit changes depending on the concentration of the detection target molecules. The detector 52 extracts, as a voltage signal or a current signal, the resistance value of the sensing unit of the gas sensor 11, and detects the detection target molecules contained in gas in the sensor chamber 100 based on the resistance value of the sensing unit.

The moisture measuring unit 12 is configured to measure an amount of moisture contained in gas in the sensor chamber 100. The amount of moisture contained in gas may be obtained by measuring a temperature and a humidity of gas. The moisture measuring unit 12 of the present embodiment includes a temperature and humidity sensor to measure the temperature and the humidity of gas in the sensor chamber 100. The moisture measuring unit 12 obtains the amount of moisture contained in gas based on measuring results relating to the temperature and the humidity, and then outputs a measuring result relating to the amount of moisture to the detector 52. While the reference gas G2 is supplied into the sensor chamber 100, the moisture measuring unit 12 measures the amount of moisture contained in the reference gas G2 after passing through the filter unit 20. In other words, a processing of measuring the amount of moisture contained in the reference gas G2 (it is also referred to as a "moisture measuring processing") includes measuring the amount of moisture contained in the reference gas G2 after passing through the filter unit 20. More specifically, the moisture measuring processing includes measuring the amount of moisture contained in the reference gas G2 based on the measuring results relating to the temperature and the humidity of the reference gas G2 in the reference gas supply passage R2 in which the reference gas G2 flows after passing through the filter unit 20.

The housing 10 is, for example, formed of a synthetic resin material or a metal material and has a box shape. The housing 10 is provided with: a first port 101 for introducing gas (the sample gas G1 or the reference gas G2) from the outside of the housing 10 to the sensor chamber 100; and a second port 102 for discharging gas from the sensor chamber 100 to the outside of the housing 10.

The first intake port P1 is connected to an input port of a particle filter 71 with a piping 61a. An output port of the particle filter 71 is connected to a first input port P11 of the three-way electromagnetic valve 75 with a piping 61b. A syringe or a collection bag containing the sample gas G1 may be connected to the first intake port P1. Alternatively, the first intake port P1 may be disposed near a source that generates the sample gas G1. The sample gas G1 introduced to the first intake port P1 is filtered by the particle filter 71 such that dust or the like with a relatively large particle diameter is removed from the sample gas, and then introduced to the first input port P11 of the three-way electromagnetic valve 75.

The second intake port P2 is connected to an input port of a particle filter 72 with a piping 62a. An output port of the particle filter 72 is connected to an input port of the two-way electromagnetic valve 73 with a piping 62b. An output port of the two-way electromagnetic valve 73 is connected to the filter unit 20 with a piping 62c.

The filter unit 20 is provided to reduce removal target components contained in the reference gas G2 input from the second intake port P2.

The filter unit 20 includes two or more kinds of target filters respectively reducing the removal target components different from each other. Since the filter unit 20 includes the two or more kinds of target filters, two or more kinds of removal target components can be reduced by the two or more kinds of target filters. In the present embodiment, for example, the filter unit 20 has a function of removing: the VOC, as the detection target molecules for the gas sensor 11; and the moisture which would affect the measuring result of the gas sensor 11. That is to say, the filter unit 20 includes, as the two or more kinds of target filters, a first filter 30 and a second filter 40. The first filter 30 is configured to reduce the detection target molecules (the VOC in the present embodiment) in the reference gas G2. The second filter 40 is configured to reduce the moisture in the reference gas G2. Since the first filter 30 and the second filter 40 respectively reduce the removal target components different from each other, the filter unit 20 with the target filters can reduce the two or more kinds of removal target components (the VOC and the moisture in the present embodiment). The target filters of the filter unit 20 are not limited to the first filter 30 reducing the VOC and the second filter 40 reducing the moisture. The filter unit 20 may include a target filter to reduce removal target components other than the VOC and the moisture (e g, ammonia, hydrogen sulfide, oxygen, carbon dioxide, or nitrogen).

The first filter 30 and the second filter 40 respectively have separation membranes 33, 43, each of which includes hollow fibers.

The first filter 30 has: a first passage 31 through which gas flows toward the sensor chamber 100 from the second intake port P2; and a second passage 32 (so-called purge line) through which gas flows toward the gas outlet port P3 from the sensor chamber 100. The separation membrane 33 is disposed between the first passage 31 and the second passage 32 in the first filter 30. The first filter 30 reducing the VOC has the separation membrane 33 made of the silicone-based synthetic resin hollow fibers, for example.

Similarly, the second filter 40 has: a first passage 41 through which gas flows toward the sensor chamber 100 from the second intake port P2; and a second passage 42 (so-called purge line) through which gas flows toward the gas outlet port P3 from the sensor chamber 100. The separation membrane 43 is disposed between the first passage 41 and the second passage 42 in the second filter 40. The second filter 40 has the separation membrane 43 made of the fluorine-based synthetic resin hollow fibers, for example.

The first passage 31 of the first filter 30 has: one end connected to the output port of the two-way electromagnetic valve 73 with the piping 62c; and the other end connected to one end of the first passage 41 of the second filter 40 with a piping 62d. The other end of the first passage 41 of the second filter 40 is connected to an input port of a check valve 74 with a piping 62e. An output port of the check valve 74 is connected to a second input port P12 of the three-way electromagnetic valve 75 with a piping 62f. An output port P13 of the three-way electromagnetic valve 75 is connected to the first port 101 of the housing 10 with a piping 63. In the present embodiment, the first filter 30 and the second filter 40 are disposed between the reference gas inlet port (the second intake port P2) and the sensor chamber 100 such that the first filter 30 is positioned between the reference gas inlet port and the second filer 40. Accordingly, the reference gas G2 can be caused to pass through the second filter 40 after the detection target molecules in the reference gas G2 are reduced by the first filter 30.

The second port 102 of the housing 10 is connected to an input port of the electromagnetic proportional control valve 76 with a piping 64a. An output port of the electromagnetic proportional control valve 76 is connected to an input port of a check valve 77 with a piping 64b. The electromagnetic proportional control valve 76 is a variable orifice that is capable of adjusting the throttling amount. The throttling amount of the electromagnetic proportional control valve 76 is controlled by an electrical signal (e.g., a current signal) received from the controller 51. An output port of the check valve 77 is connected to an input port P23 of the three-way electromagnetic valve 78 with a piping 64c. A first output port P21 of the three-way electromagnetic valve 78 is connected to one end of the second passage 42 of the second filter 40 with a piping 65a. The other end of the second passage 42 of the second filter 40 is connected to one end of the second passage 32 of the first filter 30 with a piping 65b. The other end of the second passage 32 is connected to an input port of a check valve 79 with a piping 65c. An output port of the check valve 79 is connected to an intake port of the air pump 90 with a piping 65d. A discharge port of the air pump 90 is connected to the gas outlet port P3 with a piping 67.

The second output port P22 of the three-way electromagnetic valve 78 is connected to the piping 65d with a piping 66.

The pipings 61a to 61b, 62a to 62f, 63, 64a to 64c, 65a to 65d, 66 and 67 of the present embodiment may be synthetic resin pipings, metal pipings, or synthetic resin tubes having flexibility. The gas detection system 1 of the present embodiment is configured by a pneumatic circuit and the processing unit 50 illustrated in FIG. 1 being accommodated in a casing.

The gas detection system 1 of the present embodiment includes, as gas supply passages to the sensor chamber 100: a sample gas supply passage R1 to supply the sample gas G1 from the first intake port P1 to the sensor chamber 100; and a reference gas supply passage R2 to supply the reference gas G2 from the second intake port P2 to the sensor chamber 100.

The sample gas supply passage R1 is a flow path in which gas flows from the first intake port P1 to the sensor chamber 100 via the piping 61a, the particle filter 71, the piping 61b, the three-way electromagnetic valve 75 and the piping 63 in that order. The sample gas supply passage R1 illustrated in FIG. 1 is a flow path in which gas does not pass through the filter unit 20, and this flow path is also referred to as a "first sample gas supply passage R1A." In other words, the gas detection system 1 includes the first sample gas supply passage R1A disposed to supply the sample gas G1 to the sensor chamber 100 (the gas sensor 11) not through the filter unit 20. In the first sample gas supply processing for supplying the sample gas G1, the sample gas G1 is supplied to the sensor chamber 100 through the first sample gas supply passage R1A.

The reference gas supply passage R2 is a flow path in which gas flows from the second intake port P2 to the sensor chamber 100 via the piping 62a, the particle filter 72, the piping 62b, the two-way electromagnetic valve 73, the piping 62c, the first passage 31 of the first filter 30, the piping 62d, the first passage 41 of the second filter 40, the piping 62e, the check valve 74, the piping 62f, the three-way electromagnetic valve 75 and the piping 63 in that order.

The gas detection system 1 includes, as passages for discharging gas from the sensor chamber 100: a first discharge passage R3 through which gas is discharged from the gas outlet port P3 to the outside, after flowing out of the sensor chamber 100 and passing through the filter unit 20; and a second discharge passage R4 through which gas is discharged from the gas outlet port P3 to the outside without passing through the filter unit 20, after flowing out of the sensor chamber 100.

The first discharge passage R3 is a flow path in which gas flows out of the sensor chamber 100 and is discharged from the gas outlet port P3 to the outside via the piping 64a, the electromagnetic proportional control valve 76, the piping 64b, the check valve 77, the piping 64c, the three-way electromagnetic valve 78, the piping 65a, the second passage 42 of the second filter 40, the piping 65b, the second passage 32 of the first filter 30, the piping 65c, the check valve 79, the piping 65d, the air pump 90 and the piping 67 in that order.

The second discharge passage R4 is a flow path in which gas flows out of the sensor chamber 100 and is discharged from the gas outlet port P3 to the outside via the piping 64a, the electromagnetic proportional control valve 76, the piping 64b, the check valve 77, the piping 64c, the three-way electromagnetic valve 78, the piping 66, the piping 65d, the air pump 90 and the piping 67 in that order.

The gas detection system 1 is configured to discharge the reference gas G2 by causing the reference gas G2 to flow through the first discharge passage R3 in which gas passes through the filter unit 20 from the sensor chamber 100. In other words, the first discharge passage R3 is used as a reference gas discharge passage. That is to say, the gas detection system 1 causes the reference gas G2 supplied to the sensor chamber 100 to pass through the second filter 40 and the first filter 30 in that order, and then discharges the reference gas G2.

Also, the gas detection system 1 is configured to discharge the sample gas G1 by causing the sample gas G1 to flow through the second discharge passage R4 in which gas does not pass through the filter unit 20 after flowing out of the sensor chamber 100. In other words, the second discharge passage R4 is used as a sample gas discharge passage. The sample gas discharge passage (the second discharge passage R4) illustrated in FIG. 1 is a flow path in which gas does not pass through the filter unit 20, and this flow path is also referred to as a "first sample gas discharge passage R4A." In the present embodiment, the gas detection system 1 discharges the sample gas G1, introduced into the sensor chamber 100, through the first sample gas discharge passage R4A. The first sample gas discharge passage R4A is disposed to connect the sensor chamber 100 and the gas outlet port P3 for discharging at least the sample gas G1 without passing through the filter unit 20.

(2.2) Operation (2.2.1) Detection Operation

Hereinafter, an exemplary operation about how the gas detection system 1 of the present embodiment detects the detection target molecules in the sample gas G1 will be described. In case of detecting the detection target molecules in the sample gas G1, the gas detection system 1 supplies, to the gas sensor 11, the reference gas G2 where the detection target molecules are reduced (i.e., where the detection target molecules hardly exist) to acquire an output value of the gas sensor 11, as a reference value. Then, the gas detection system 1 supplies the sample gas G1 to the gas sensor 11 and detects the detection target molecules in the sample gas G1 based on the above-mentioned reference value and an output value of the gas sensor 11 obtained by supplying the sample gas G1.

Hereinafter, the detection operation of the gas detection system 1 will be explained with reference to a flowchart of FIG. 2.

The controller 51 starts the detection operation, switches the two-way electromagnetic valve 73 to the open state, and activates the air pump 90 (Step S1). The second input port P12 of the three-way electromagnetic valve 75 is a normally open type, and the first output port P21 of the three-way electromagnetic valve 78 is also a normally open type. Accordingly, the reference gas G2 introduced from the second intake port P2 passes through the reference gas supply passage R2 and is introduced into the sensor chamber 100. Then the reference gas G2 discharged from the sensor chamber 100 passes through the first discharge passage R3 and is discharged from the gas outlet port P3 to the outside.

The controller 51 of the present embodiment operates so as to alternately repeat: a first time period for supplying the reference gas G2 to the sensor chamber 100 to acquire the reference value; and a second time period for supplying the sample gas G1 to the sensor chamber 100 to detect the detection target molecules.

In the first time period (if the answer is Yes in Step S2), the controller 51 controls the two-way electromagnetic valve 73 to be switched to the open state, and controls the three-way electromagnetic valve 75 such that the second input port P12 is switched to the open state and the first input port P11 is switched to the close state, and controls the three-way electromagnetic valve 78 such that the first output port P21 is switched to the open state and the second output port P22 is switched to the close state (Step S3). Accordingly, the gas flow path is switched such that the reference gas G2 flows through the reference gas supply passage R2 from the second intake port P2 and is introduced to the sensor chamber 100, and then flows out of the sensor chamber 100 and flows through the first discharge passage R3 (the reference gas discharge passage) and is discharged to the outside. In that state, when the controller 51 starts the operation of the air pump 90, the reference gas G2 is sucked from the second intake port P2, and flows through the reference gas supply passage R2 and is introduced to the sensor chamber 100, and then flows through the first discharge passage R3 and is discharged from the gas outlet port P3 to the outside.

In the first time period, the reference gas G2 introduced to the second intake port P2 is filtered by the particle filter 72 such that dust or the like with a relatively large particle diameter is removed, and then passes through the two-way electromagnetic valve 73 and is supplied to the first passage 31 of the first filter 30. When the reference gas G2 flows to the first passage 31 of the first filter 30, the VOC (the removal target components) in the reference gas G2 permeates the separation membrane 33 due to that the pressure in the second passage 32 is less than that in first passage 31. The VOC permeated the separation membrane 33 is diffused in the separation membrane 33 and moved toward the second passage 32. Then, the VOC is desorbed from the separation membrane 33, and moved into the second passage 32. The VOC moved in the second passage 32 passes through the piping 65c, the check valve 79, the piping 65d, the air pump 90 and the piping 67 in that order from the second passage 32, and then is discharged from the gas outlet port P3 to the outside.

When the reference gas G2 passes through the first passage 31 of the first filter 30 and flows to the first passage 41 of the second filter 40 through the piping 62d, the moisture (the removal target components) in the reference gas G2 permeates the separation membrane 43 due to that the pressure in the second passage 42 is less than that in first passage 41. The moisture permeated the separation membrane 43 is diffused in the separation membrane 43 and moved toward the second passage 42. Then, the moisture is desorbed from the separation membrane 43, and moved into the second passage 42. The moisture moved in the second passage 42 passes through the piping 65b, the second passage 32 of the first filter 30, the piping 65c, the check valve 79, the piping 65d, the air pump 90 and the piping 67 in that order from the second passage 42, and then is discharged from the gas outlet port P3 to the outside.

Thus, the reference gas G2 introduced to the second intake port P2 passes through the first filter 30 and the second filter 40 in that order, and the VOC and the moisture in the reference gas G2 are accordingly reduced, and then the reference gas G2 is sent to the sensor chamber 100 of the housing 10. More specifically, in the reference gas supply processing supplying the reference gas G2 to the gas sensor 11 through the filter unit 20, the reference gas G2 is caused to pass through the first filter 30 and then pass through the second filter 40, and supplied to the sensor chamber 100 (the gas sensor 11). Therefore, the reference gas G2, after the VOC and moisture are reduced, is supplied to the gas sensor 11, which can obtain the output value of the gas sensor 11 in that state, as the reference for the VOC that is the detection target molecules. Furthermore, the reference gas G2, after the moisture is reduced, is supplied to the gas sensor 11, which can reduce a chance that the gas sensor 11 deteriorates due to the moisture included in the reference gas G2 or the measuring result varies.

The separation membrane 43 of the second filter 40 is made of the fluorine-based synthetic resin hollow fibers, and the fluorine-based synthetic resin has the property of being easily deteriorated by the VOC. In the present embodiment, the reference gas G2, after the VOC is reduced by the first filter 30, is supplied to the second filter 40, which can reduce a chance that the separation membrane 43 of the second filter 40 is deteriorated by the VOC. In addition, the first filter 30 and the second filter 40 reduce the removal target components in the reference gas G2, using the separation membranes 33 and 43 each of which is made of the hollow fibers. Therefore, replacement of a filter material is not required, unlike a filter using a filter material such as activated carbon, and maintenance-free can be realized.

In the present embodiment, the moisture controller 512 of the controller 51 adjusts the throttling amount of the electromagnetic proportional control valve 76 in the first time period based on the amount of moisture in the reference gas G2, measured by the moisture measuring unit 12, to perform the moisture adjustment processing for adjusting the amount of moisture in the reference gas G2 (Step S4).

For example, the moisture controller 512 compares an absolute humidity of the reference gas G2 in the sensor chamber 100, measured by the moisture measuring unit 12, with a predetermined reference humidity. The reference humidity is e.g., 1 g/m$^3$. The reference humidity may be modified as appropriate according to use conditions and so on.

If the absolute humidity of the reference gas G2 in the sensor chamber 100 is greater than the reference humidity, the moisture controller 512 controls an orifice diameter of the electromagnetic proportional control valve 76 to be adjusted to a first opening diameter. The first opening diameter is set as an opening diameter less than the orifice diameter in case that the absolute humidity of the reference gas G2 is equal to or less than the reference humidity. The moisture controller 512 adjusts the orifice diameter of the electromagnetic proportional control valve 76 to the first opening diameter, which increases a difference between pressures at the front and rear of the electromagnetic proportional control valve 76 and reduces the pressure in the second passage 42 of the second filter 40. It accordingly increases a difference between pressures in the first passage 41 and the second passage 42, which also increases, in the second filter 40, the amount of moisture permeating the separation membrane 43 from the first passage 41 to move to the second passage 42. Consequently, the amount of moisture in the reference gas G2 is reduced in the sensor chamber 100 to be closer to the predetermined reference humidity.

On the other hand, if the absolute humidity of the reference gas G2 in the sensor chamber 100 is equal to or less than the reference humidity, the moisture controller 512 controls the orifice diameter of the electromagnetic proportional control valve 76 to be adjusted to a second opening diameter greater than the first opening diameter. In this case, the difference between pressures at the front and rear of the electromagnetic proportional control valve 76 is further reduced and the pressure in the second passage 42 of the second filter 40 is further increased, compared with when the orifice diameter of the electromagnetic proportional control valve 76 is at the first opening diameter. It accordingly reduces the difference between pressures in the first passage 41 and the second passage 42, which also reduces, in the second filter 40, the amount of moisture permeating the separation membrane 43 from the first passage 41 to move to the second passage 42. Consequently, the amount of moisture in the reference gas G2 is increased in the sensor chamber 100 to be closer to the predetermined reference humidity.

Thus, the moisture controller 512 adjusts the difference between pressures in the first passage 41 and the second passage 42 of the second filter 40, thereby keeping the absolute humidity of the reference gas G2 in the sensor chamber 100 to be the reference humidity. The detector 52 acquires the reference value for the concentration of the detection target molecules based on the output value of the gas sensor 11 in this state (Step S5). That is to say, the moisture controller 512, in the moisture adjustment processing, adjusts a pressure difference of the separation membrane 43 of the second filter 40. In the first time period, the quality of the reference gas G2 can be stably controlled by adjusting the amount of moisture in the reference gas G2, which can suppress variation in the reference value for the concentration of the VOC as the detection target molecules. Accordingly, the VOC in the sample gas G1 can be measured more accurately. In this way, the gas detection system 1, in the first time period, performs the reference gas supply processing that includes causing the reference gas G2, as the reference to the concentration of the detection target molecules in the sample gas G1, to pass through the filter unit 20, which is configured to reduce the removal target components in the reference gas G2, to supply the reference gas G2 to the sensor chamber 100 in which the gas sensor 11 is housed (Steps S3 to S5).

Next, the operation of the gas detection system 1 in the second time period will be explained. In the second time period (if the answer is "No" in Step S2), the controller 51 controls the two-way electromagnetic valve 73 to be switched to the close state, and controls the three-way electromagnetic valve 75 such that the first input port P11 is switched to the open state and the second input port P12 is switched to the close state, and controls the three-way electromagnetic valve 78 such that the first output port P21 is switched to the close state and the second output port P22 is switched to the open state (Step S6). Accordingly, the gas flow path is switched such that the sample gas G1 flows through the sample gas supply passage R1 from the first intake port P1 and is introduced to the sensor chamber 100, and then flows out of the sensor chamber 100 and flows through the second discharge passage R4 (the sample gas discharge passage) and is discharged to the outside. In that state, when the controller 51 starts the operation of the air pump 90, the sample gas G1 is sucked from the first intake port P1, and flows through the sample gas supply passage R1 and is introduced to the sensor chamber 100, and then flows through the second discharge passage R4 and is discharged from the gas outlet port P3 to the outside.

In the second time period, the detector 52 obtains the output value of the gas sensor 11 (Step S7), and performs a processing to detect the detection target molecules (the VOC as the odor component molecules in the present embodiment) in the sample gas G1 based on the output value and the reference value acquired in the first time period (Step S8). In the present embodiment, the detector 52 may detect a state about whether the detection target molecules are present or absent, may detect the concentration of the detection target molecules, or may detect a state about whether the concentration of the detection target molecules is greater than or less than a prescribed setting value. In the second time period, the sample gas G1 is discharged through the second discharge passage R4 bypassing the filter unit 20. Accordingly, the sample gas G1 (which has not passed through the first filter 30) also does not pass through the second filter 40, which can suppress the deterioration of the second filter 40 due to the VOC.

The controller 51 of the gas detection system 1 repeatedly preforms the detection operation to detect the VOC in the sample gas G1 by alternately repeating the first time period and the second time period. In this case, the moisture adjustment processing (the Step S4) adjusting the amount of moisture in the reference gas G2 may be omitted as appropriate in the first time period from the second cycle of the cycles, each of which a set of the first time period and the second time period is included. Each of lengths of the first and second time periods is set as ten seconds, for example, but the lengths of the first and second time periods may be modified as appropriate. The lengths of the first and second time periods may be set to be different from each other.

As described above, the gas detection system 1 of the present embodiment includes the reference gas supply passage R2 for causing the reference gas G2 to pass through the filter unit 20 and then supplying it to the sensor chamber 100, separately from the sample gas supply passage R1 for supplying the sample gas G1 to the sensor chamber 100. The reference gas G2 introduced from the second intake port P2 is supplied to the sensor chamber 100, after the detection target molecules (the VOC in the present embodiment) and the moisture are reduced by the filter unit 20. Consequently, air in the environment can be used as the reference gas G2.

Also, the gas detection system 1 includes the second discharge passage R4 for discharging the sample gas G1 from the sensor chamber 100 without the sample gas G1 passing through the filter unit 20, separately from the first discharge passage R3 for discharging the reference gas G2 from the sensor chamber 100. Accordingly, the sample gas G1 including the detection target molecules (the VOC in the present embodiment) and the moisture is discharged to the outside without passing through the purge line (the second passages 32, 42) of the filter unit 20, which can suppress deterioration of the filter performance of the filter unit 20. For example, even when gas collected from food, or gas including moisture (e.g., exhaled breath) is used as the sample gas G1, the deterioration of the filter performance of the filter unit 20 can be suppressed by the sample gas G1 being discharged to the outside through the second discharge passage R4.

The gas detection system 1 includes the electromagnetic proportional control valve 76 disposed on the downstream side of the sensor chamber 100 and reduces the amount of gas (the sample gas G1 or the reference gas G2) flowing through the sensor chamber 100 by reducing the orifice diameter of the electromagnetic proportional control valve 76, which can therefore suppress deterioration of the filter performance of the filter unit 20 and deterioration of the gas sensor 11.

(2.2.2) Stop State

Figure 3:
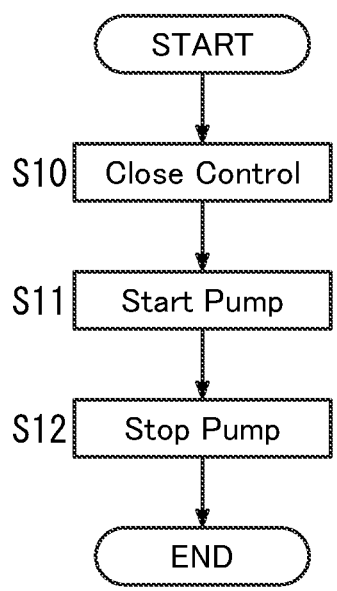
FIG. 3 is a flowchart for explaining operation in a stop state of the gas detection system.

Hereinafter, the stop state where the gas detection system 1 of the present embodiment stops the detection operation for the sample gas G1 will be explained with reference to a flowchart of FIG. 3.

In the stop state, the controller 51 controls the two-way electromagnetic valve 73 to be switched to the close state, controls the three-way electromagnetic valve 75 such that the second input port P12 is switched to the open state and the first input port P11 is switched to the close state, and controls the three-way electromagnetic valve 78 such that the first output port P21 is switched to the open state and the second output port P22 is switched to the close state (Step S10).

Thus, inflow of the outside air from the first intake port P1 is blocked by the three-way electromagnetic valve 75, also inflow of the outside air from the second intake port P2 is blocked by the two-way electromagnetic valve 73, and inflow of the outside air from the gas outlet port P3 is blocked by the check valve 79 and the three-way electromagnetic valve 78. The gas detection system 1 of the present embodiment performs a shutoff processing (Step S10) that includes shutting off the outside air toward the filter unit 20 in the stop state where the detection operation of the gas sensor 11 is stopped. In the present embodiment, the filter unit 20 is connected to the outside by two or more flow passages including the reference gas supply passage R2. The two or more flow passages including the reference gas supply passage R2 corresponds to, for example, the sample gas supply passage R1, the reference gas supply passage R2, the first discharge passage R3, the second discharge passage R4 and so on. The two or more flow passages are provided with, as shutoff elements, the two-way electromagnetic valve 73, the three-way electromagnetic valves 75, 78, and the check valve 79, respectively. In the stop state (e.g., while the power is off), the two or more flow passages are shut off by the shutoff elements. In other words, the shutoff unit CB1 includes the two or more shutoff elements disposed at the two or more flow passages, respectively. Each of the two or more shutoff elements is provided to shut-off a corresponding flow passage of the two or more flow passages between the filter unit 20 and the outside in the stop state, which can reduce a chance that the filter unit 20 is exposed to the outside air. The deterioration of the filter unit 20 can be therefore suppressed. The shutoff unit CB1 includes electromagnetic selector valve(s) (more specifically, the two-way electromagnetic valve 73 and the three-way electromagnetic valves 75, 78), which are switched to either the open state or the close state by the electromagnetic force. Therefore, each electromagnetic selector valve can be switched between the open state and the close state by receiving an electrical signal from the controller 51. Also, the shutoff unit CB1 includes the check valve 79. When the shutoff unit CB1 includes the check valve 79 as one of the shutoff elements, the gas detection system 1 has an advantage that power supply and signal line are not required, compared with a case that the shutoff unit CB1 includes an electromagnetic selector valve as one of the shutoff elements.

When the control state transitions to the stop state, while the controller 51 controls the two-way electromagnetic valve 73 to be switched to the close state, controls the three-way electromagnetic valve 75 such that the second input port P12 is switched to the open state and the first input port P11 is switched to the close state, and controls the three-way electromagnetic valve 78 such that the first output port P21 is switched to the open state and the second output port P22 is switched to the close state, the controller 51 may start the operation of the air pump 90 (Step S11) to reduce pressure in the circuit including the filter unit 20 to be less than external pressure (for example, such that the circuit is made closer to a vacuum state). When the air pump 90 is started, the check valve 79 is switched to the open state and therefore the pressure in the circuit including the filter unit 20 is reduced. The controller 51 operates the air pump 90 during a prescribed time and then stops the air pump 90 (Step S12). When the air pump 90 is stopped, the check valve 79 is switched to the close state and therefore, the pressure in the circuit portion including the filter unit 20 shut off by the shutoff unit CB1 is kept at a negative pressure. If the pressure in a circuit C1 (from the two-way electromagnetic valve 73 to the check valve 79 through the housing 10) is reduced in the stop state, the check valve 79 is hardly opened, which can reduce a chance that the filter unit 20 is exposed to the outside air.

(2.2.3) Idling Operation

In the gas detection system 1 of the present embodiment, the idling controller 511 of the controller 51 may have an idling time period for performing an idling operation to cause the reference gas G2 to flow to the filter unit 20 in the stop state. In other words, the gas detection system 1 further includes the idling controller 511 configured to switch the shutoff unit CB1 to a non-shutoff state and perform the idling operation to supply the reference gas G2 to the gas sensor 11 in the stop state.

In the idling time period, the reference gas G2 introduced from the second intake port P2 passes through the reference gas supply passage R2 and is supplied to the sensor chamber 100, and then is discharged to the outside through the first discharge passage R3 (i.e., the reference gas discharge passage). The separation membrane 43 including the hollow fibers, of the second filter 40, has the filter performance which would greatly change depending on its dry state. When the stop state is continued for a long time and the separation membrane 43 therefore contains a lot of moisture, the filter performance may be reduced. The separation membrane 43 including the hollow fibers, of the second filter 40 can be dried by causing the reference gas G2 to flow to the filter unit 20 during the idling time period in order to overcome the above problem. The filter performance of the second filter 40 can be accordingly improved.

If finding that the amount of moisture detected by the detector 52 based on the measuring result of the moisture measuring unit 12 is greater than a prescribed first threshold in the stop state, the controller 51 controls the two-way electromagnetic valve 73 to be switched to the open state and operates the air pump 90 to start the idling operation. After that if finding that the amount of moisture detected by the detector 52 is equal to or less than a prescribed second threshold, the controller 51 controls the two-way electromagnetic valve 73 to be switched to the close state and then stops the air pump 90 so as to keep at the negative pressure the pressure in the circuit portion including the filter unit 20 shut off by the shutoff unit CB1.

In this way, the gas detection system 1 performs the idling operation, if finding that the amount of moisture detected by the detector 52 is greater than the first threshold in the stop state, which can keep the second filter 40 in the dried state and can resume the detection operation using the second filter 40 kept in the dried state.

The controller 51 preferably controls the orifice diameter of the electromagnetic proportional control valve 76 such that the amount of the reference gas G2 flowing upon the idling operation is greater than the amount of the reference gas G2 flowing in the first time period upon the detection operation. In this case, the gas detection system 1 can quickly dry the filter unit 20 and finish the idling operation by causing the reference gas G2 to flow at a great flow rate during the idling time period.

In the present embodiment, the controller 51 decides a start timing and an end timing of the idling operation based on the measuring result of the moisture measuring unit 12. Alternatively, the controller 51 may decide the start timing and the end timing of the idling operation based on the output value of the gas sensor 11 which changes depending on the amount of moisture in gas. The moisture measuring unit 12 of the gas detection system 1 is optional, if the controller 51 decides the start timing and the end timing of the idling operation based on the output value of the gas sensor 11 which changes depending on the amount of moisture in gas. The controller 51 estimates the amount of moisture in gas based on the output value of the gas sensor 11 in the first time period and controls the operation of the air pump 90 based on the estimated result relating to the amount of moisture, which can keep the quality of the reference gas G2 stably and accordingly reduce variation in the detection result relating to the sample gas G1. The characteristics of the gas sensor 11 may change or deteriorate with the lapse of time, but the gas detection system 1 can return the characteristics of the gas sensor 11 to the initial state by supplying to the gas sensor 11 the reference gas G2 in which the VOC and the moisture are reduced during the idling time period.

(3) Variations

The embodiment described above is only an exemplary one of various embodiments of the present disclosure and should not be construed as limiting. The exemplary embodiment may be readily modified in various manners depending on a design choice or any other factor, as long as the purpose of the present disclosure can be attained. The functions similar to the gas detection system 1 may also be implemented as, for example, a control method for the gas detection system 1, a computer program, or a non-transitory storage medium that stores the computer program. A control method for a gas detection system 1, according to an aspect, includes the reference gas supply processing described above. A (computer) program according to an aspect is a computer program designed to cause a computer system to execute the reference gas supply processing described above.

Hereinafter, variations of the exemplary embodiment described above will be listed. The variations to be described below may be adopted in combination as appropriate.

The gas detection system 1 according to the present disclosure includes a computer system, for example, as the processing unit 50. The computer system may include a processor and a memory as principal hardware components. The functions of the gas detection system 1 may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be implemented as a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very large-scale integrated circuit (VLSI), and an ultra-large scale integrated circuit (ULSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be integrated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Also, the plurality of functions of the gas detection system 1 are integrated together in a single housing, but this is not an essential configuration for the gas detection system 1. Alternatively, the plurality of functions of the gas detection system 1 may be distributed in multiple different housings. Still alternatively, at least some functions of the gas detection system 1 (e.g., some functions of the processing unit 50) may be implemented as a cloud computing system as well.

In the foregoing embodiment, the phrase "greater than" used in a situation where two values such measuring data being compared with each other may be replaced with the phrase "equal to or greater than." That is to say, it is arbitrarily changeable depending on selection of the reference value or the threshold whether or not a case where the two values are equal to each other should be covered. Therefore, from a technical point of view, there is no difference between the phrase "greater than" and the phrase "equal to or greater than." Similarly, the phrase "equal to or less than" may be replaced with the phrase "less than" as well.

Figure 4:
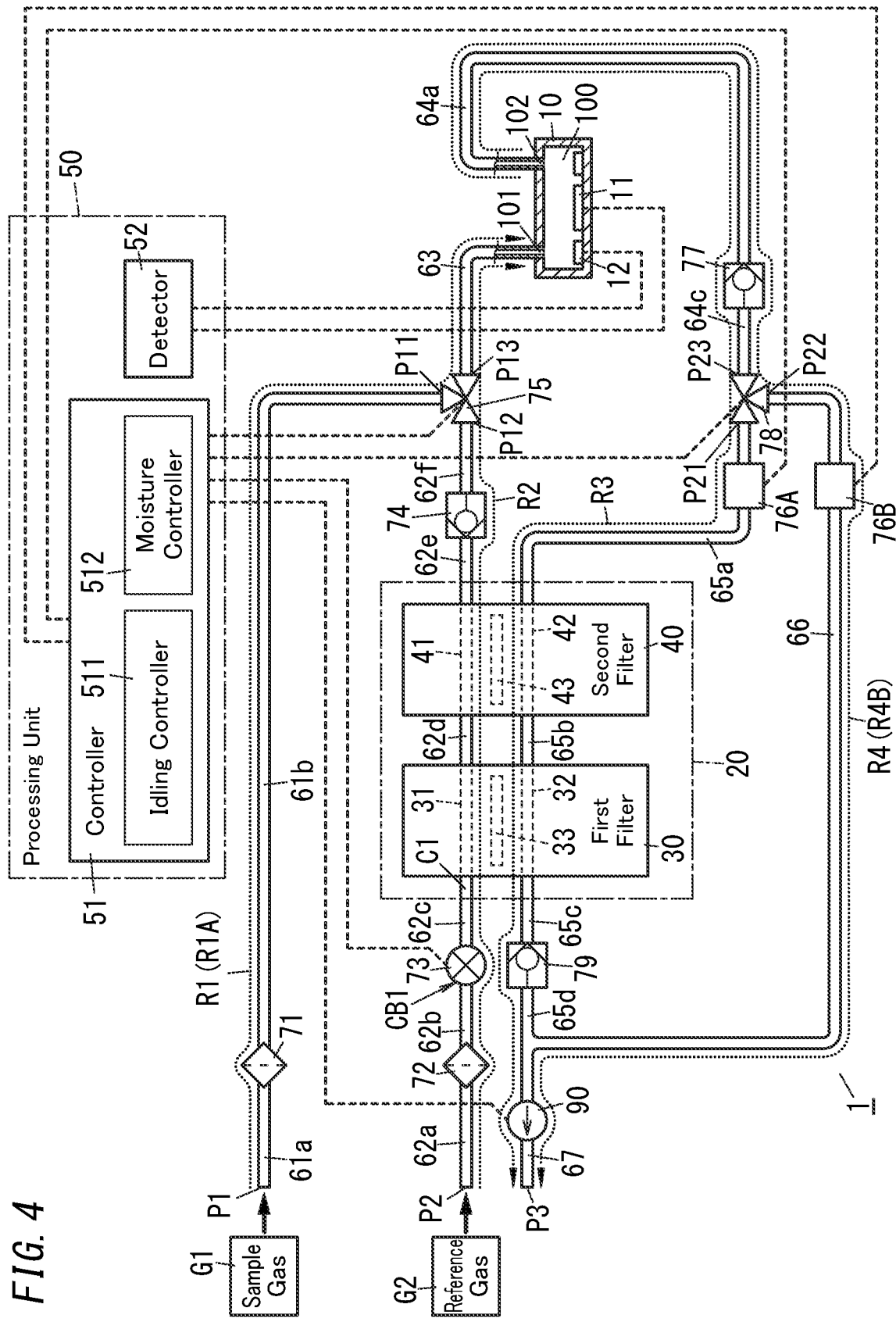
FIG. 4 is a schematic system configuration diagram showing a first variation of the gas detection system.

In the foregoing embodiment, the electromagnetic proportional control valve 76 is disposed on the upstream side of the three-way electromagnetic valve 78 (i.e., on the side of the housing 10). However, this is only an example and should not be construed as limiting. As a first variation illustrated in FIG. 4, electromagnetic proportional control valves 76A, 76B may be respectively disposed on the downstream sides of the first output port P21 and the second output port P22 of the three-way electromagnetic valve 78, instead of the electromagnetic proportional control valve 76. That is to say, the electromagnetic proportional control valve 76A may be disposed between the filter unit 20 and the first output port P21 of the three-way electromagnetic valve 78, and the amount of gas flowing through the first discharge passage R3 may be controlled by the electromagnetic proportional control valve 76A. Also, the electromagnetic proportional control valve 76B may be disposed between a joint part of the pipings 66, 65d and the second output port P22 of the three-way electromagnetic valve 78, and the amount of gas flowing through the second discharge passage R4 may be controlled by the electromagnetic proportional control valve 76B.

Figure 5:
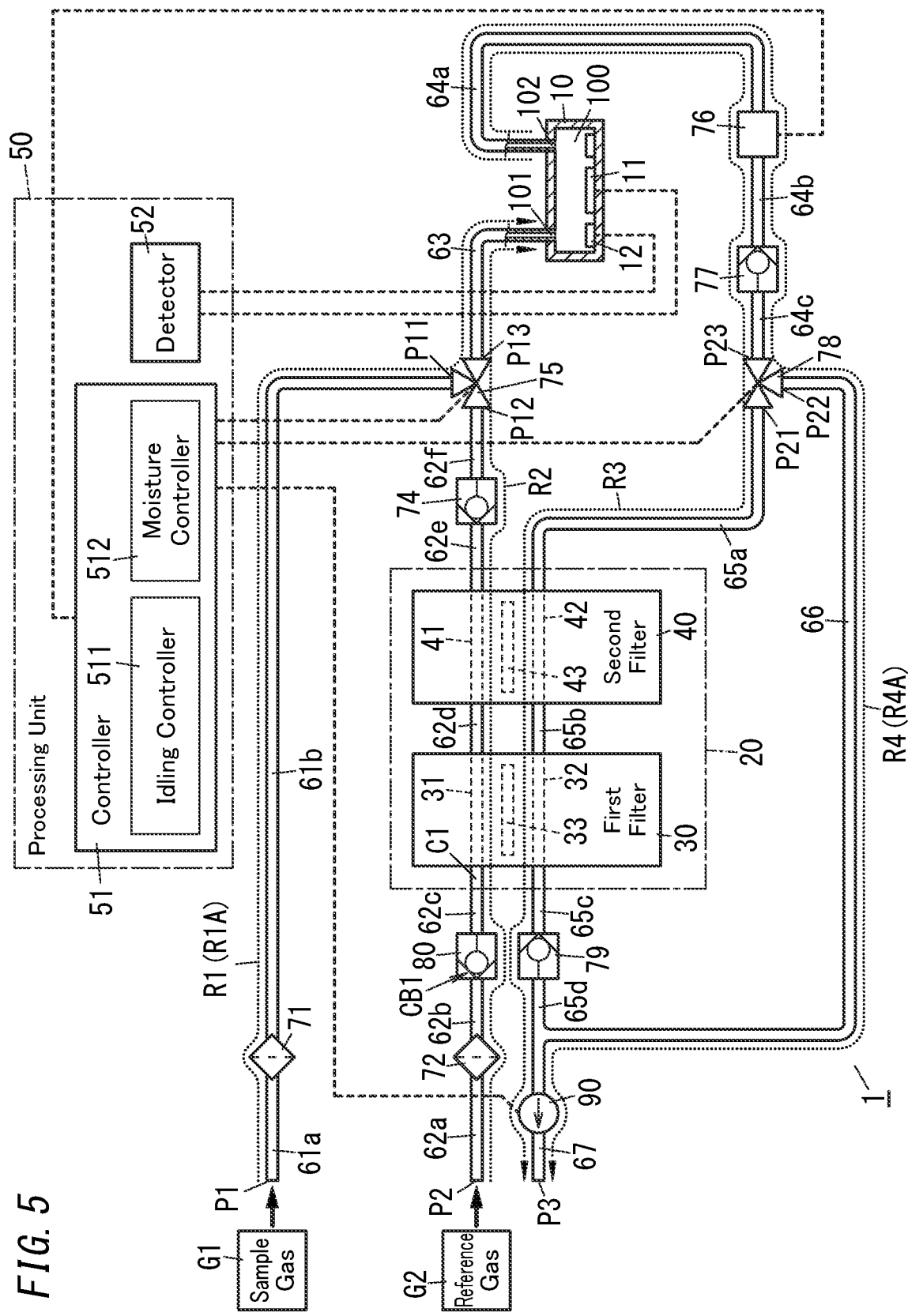
FIG. 5 is a schematic system configuration diagram showing a second variation of the gas detection system.

In the foregoing embodiment, the two-way electromagnetic valve 73 is disposed between the second intake port P2 and the filter unit 20. However, this is only an example and should not be construed as limiting. As a second variation illustrated in FIG. 5, a check valve 80 may be connected, instead of the two-way electromagnetic valve 73. Using the check valve 80 instead of the two-way electromagnetic valve 73 can contribute to omission of wiring for connecting the two-way electromagnetic valve 73 to the power supply and the controller 51.

Figure 6:
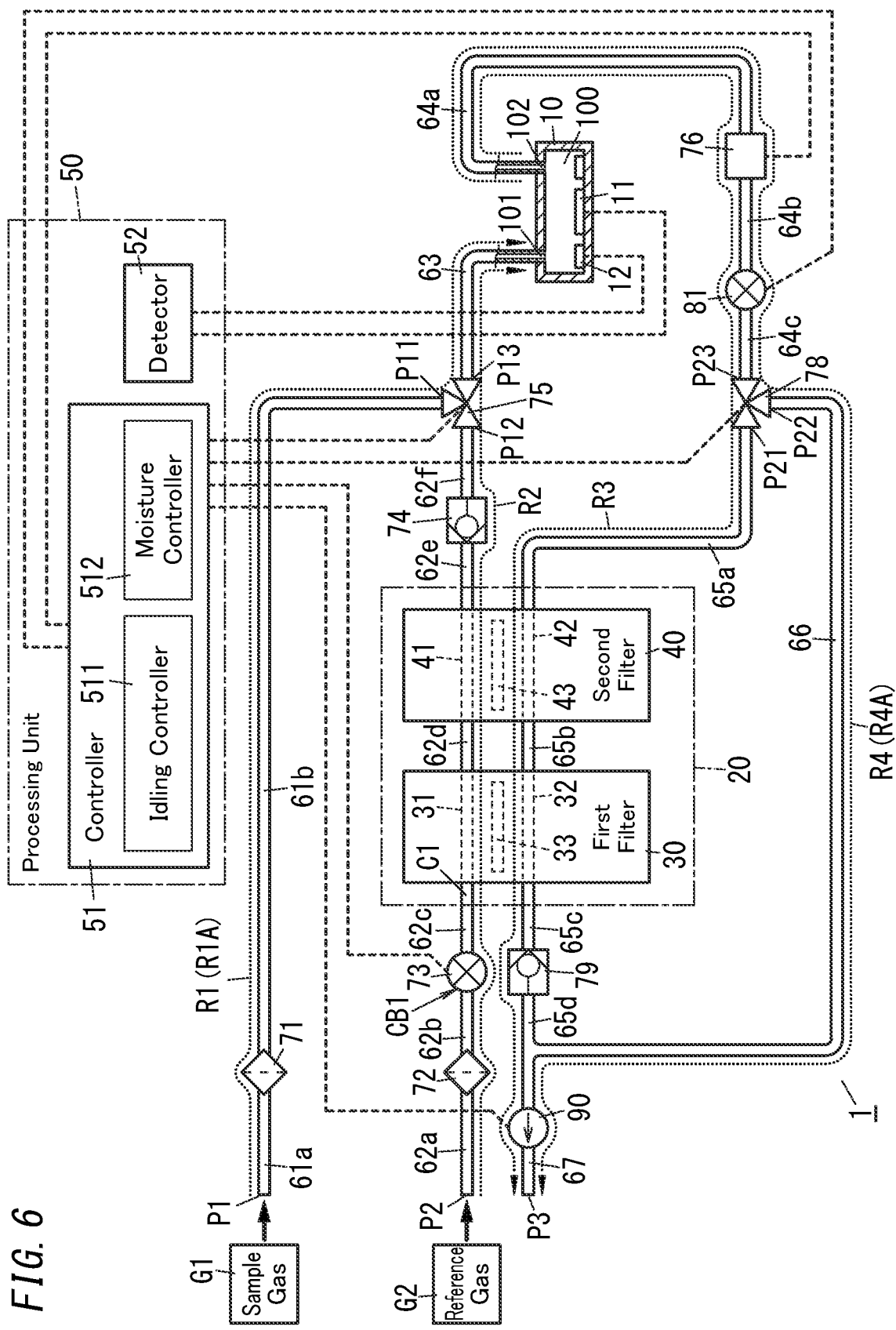
FIG. 6 is a schematic system configuration diagram showing a third variation of the gas detection system.

In the foregoing embodiment, the check valve 77 is disposed between the electromagnetic proportional control valve 76 and the three-way electromagnetic valve 78. However, this is only an example and should not be construed as limiting. As a third variation illustrated in FIG. 6, a two-way electromagnetic valve 81 may be disposed, instead of the check valve 77. Using the two-way electromagnetic valve 81 instead of the check valve 77 can prevent the two-way electromagnetic valve 81 from being unintentionally switched to the open state and can improve airtightness of the circuit portion including the filter unit 20 in the stop state. In the foregoing embodiment, two-way electromagnetic valves may be used instead of the check valves 74 and 79.

Figure 7:
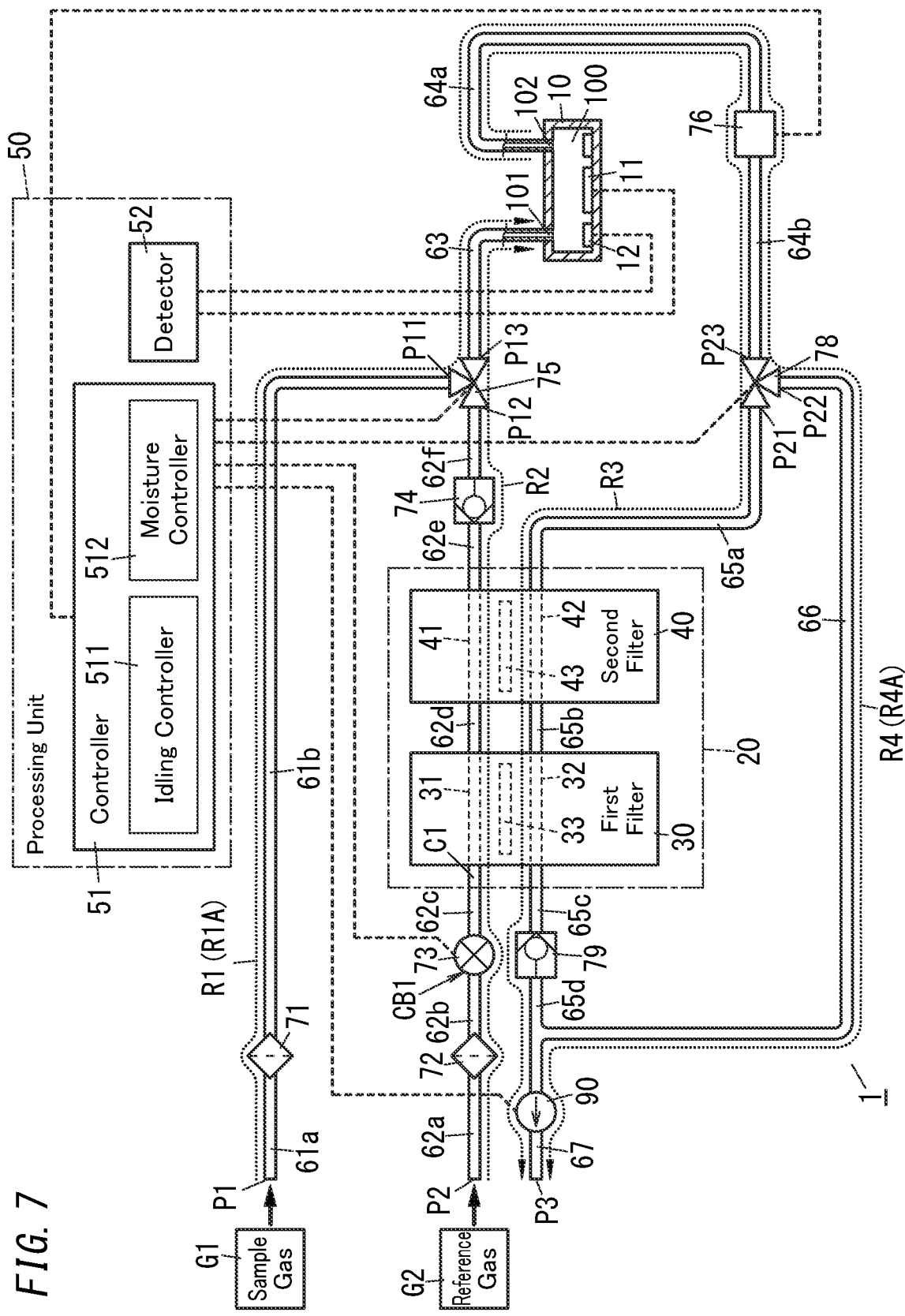
FIG. 7 is a schematic system configuration diagram showing a fourth variation of the gas detection system.
Figure 8:
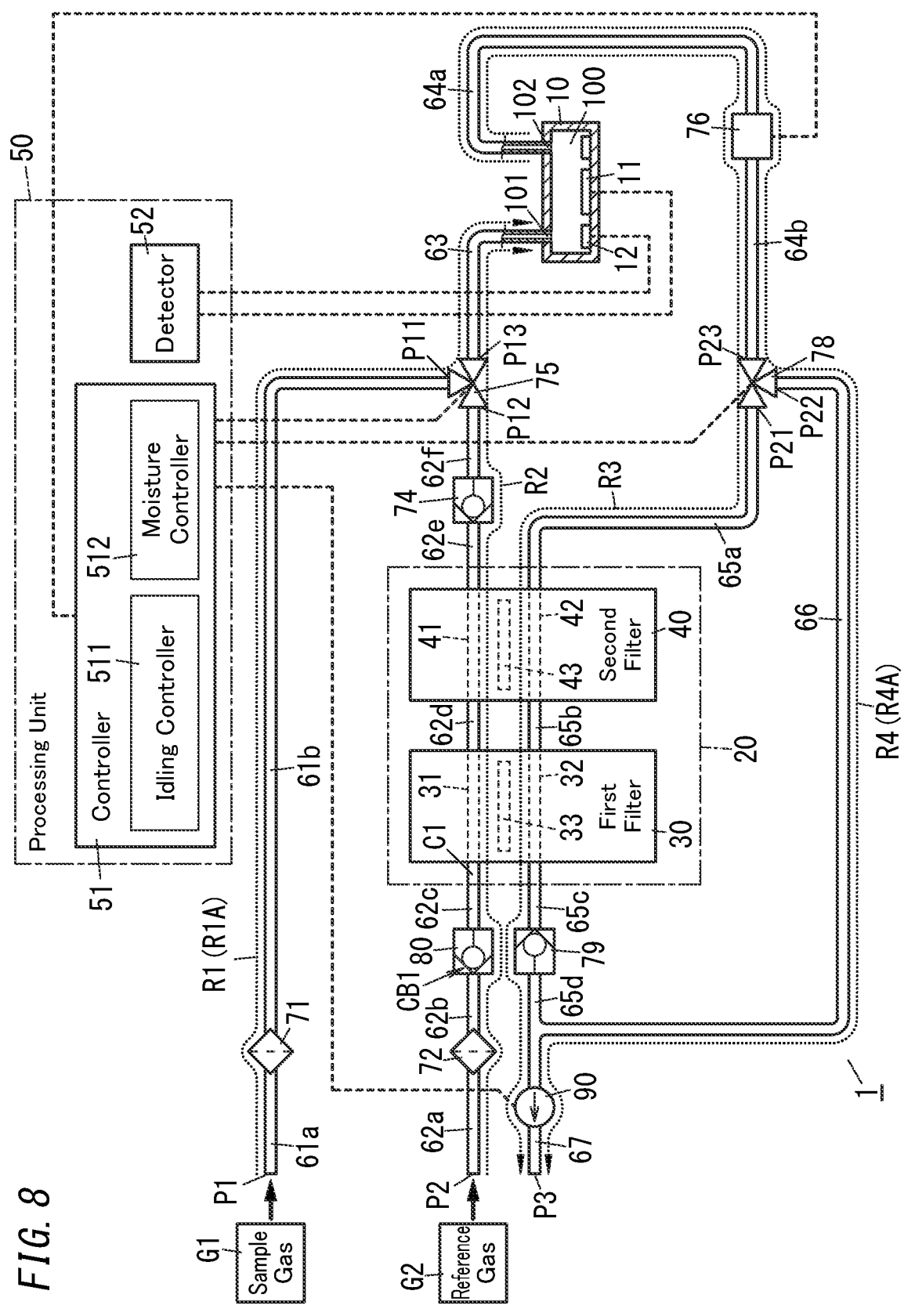

In the foregoing embodiment, the check valve 77 may be omitted, which is connected between the electromagnetic proportional control valve 76 and the three-way electromagnetic valve 78. That is to say, as a fourth variation illustrated in FIG. 7, the output port of the electromagnetic proportional control valve 76 may be directly connected to the input port P23 of the three-way electromagnetic valve 78 via the piping 64b, which can contribute to omission of the check valve 77. Also in the gas detection system 1 illustrated in FIG. 5 described above, the check valve 77 may be omitted, which is connected between the electromagnetic proportional control valve 76 and the three-way electromagnetic valve 78. That is to say, as a fifth variation illustrated in FIG. 8, the output port of the electromagnetic proportional control valve 76 may be directly connected to the input port P23 of the three-way electromagnetic valve 78 via the piping 64b, which can contribute to omission of the check valve 77.

Figure 9:
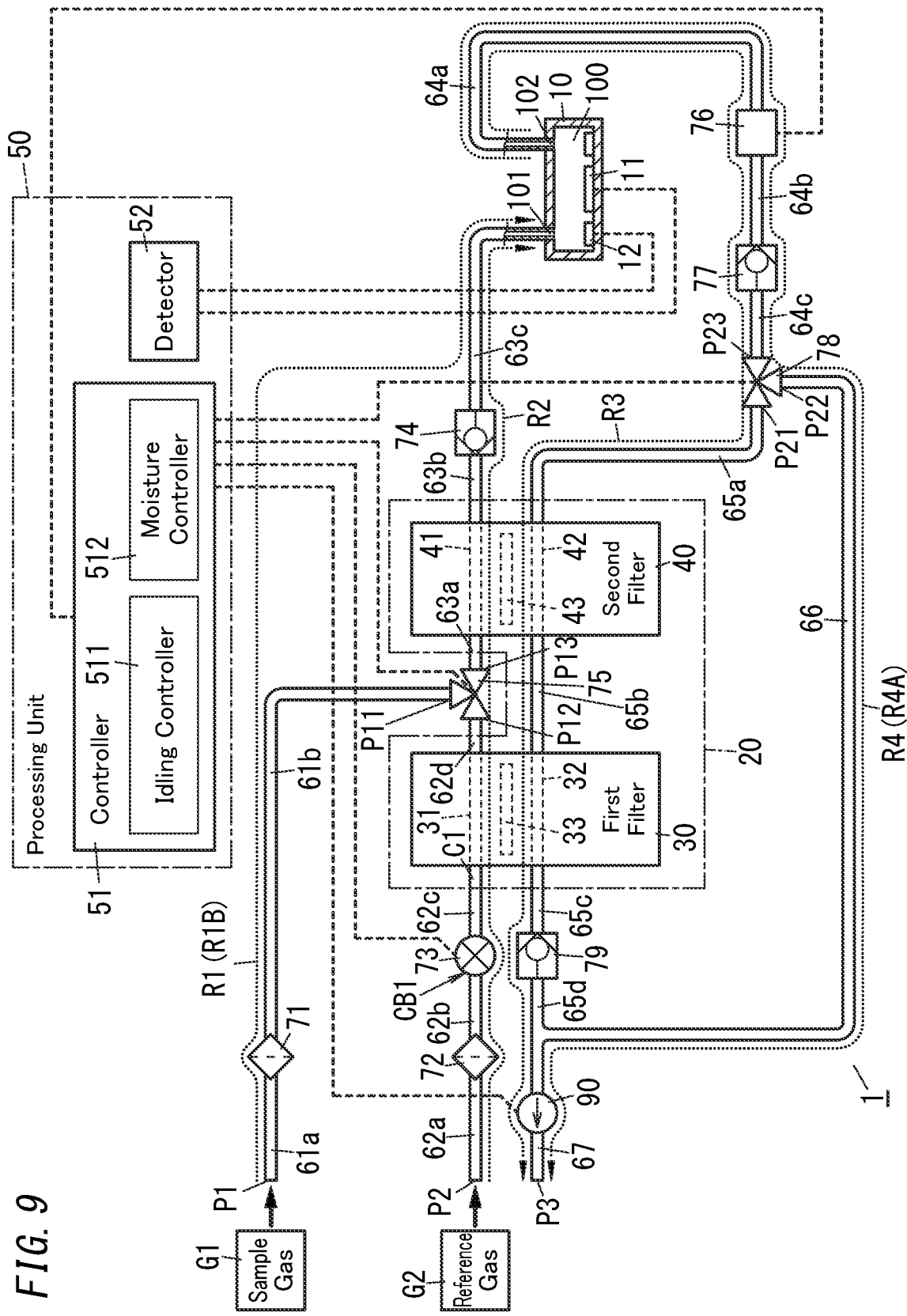
FIG. 9 is a schematic system configuration diagram showing a sixth variation of the gas detection system.

In the foregoing embodiment, the sample gas supply passage R1 is provided not to pass through the filter unit 20. However, this is only an example and should not be construed as limiting. As a sixth variation illustrated in FIG. 9, the sample gas supply passage R1 may be provided so as to pass through only the second filter 40 for moisture, of the filter unit 20.

In the gas detection system 1 according to the sixth variation, the second input port P12 of the three-way electromagnetic valve 75 is connected to the first passage 31 of the first filter 30 with the piping 62d, and the output port P13 of the three-way electromagnetic valve 75 is connected to one end of the first passage 41 of the second filter 40 with the piping 63a. Furthermore, the other end of the first passage 41 of the second filter 40 is connected to the input port of the check valve 74 with the piping 63b, and the output port of the check valve 74 is connected to the first port 101 of the housing 10 with the piping 63c.

The operation of the gas detection system 1 according to the sixth variation is similar to the operation of the gas detection system 1 in the foregoing embodiment, except for the processing (refer to Step S6 in FIG. 2) supplying the sample gas G1 to the sensor chamber 100.

Since the reference gas supply processing (refer to Step S3 in FIG. 2) supplying the reference gas G2 to the sensor chamber 100 in the gas detection system 1 according to the sixth variation is similar to that in the gas detection system 1 in the foregoing embodiment, the explanation thereof will be omitted. As described above, the reference gas G2 supplied to the sensor chamber 100 flows through the reference gas discharge passage (the first discharge passage R3) and is discharged from the gas outlet port P3 to the outside. The reference gas supply passage R2 connects the sensor chamber 100 and the reference gas inlet port (the second intake port P2) from which the reference gas G2 is introduced. The reference gas supply passage R2 causes the reference gas G2 introduced from the reference gas inlet port to pass through the first filter 30 and the second filter 40 in that order and then introduces it to the sensor chamber 100. The reference gas discharge passage (the first discharge passage R3) connects the sensor chamber 100 and the gas outlet port P3 for discharging at least the reference gas G2. The first discharge passage R3 causes the reference gas G2 discharged from the sensor chamber 100 to pass through the second filter 40 and the first filter 30 in that order and then discharges it from the gas outlet port P3.

Figure 2:
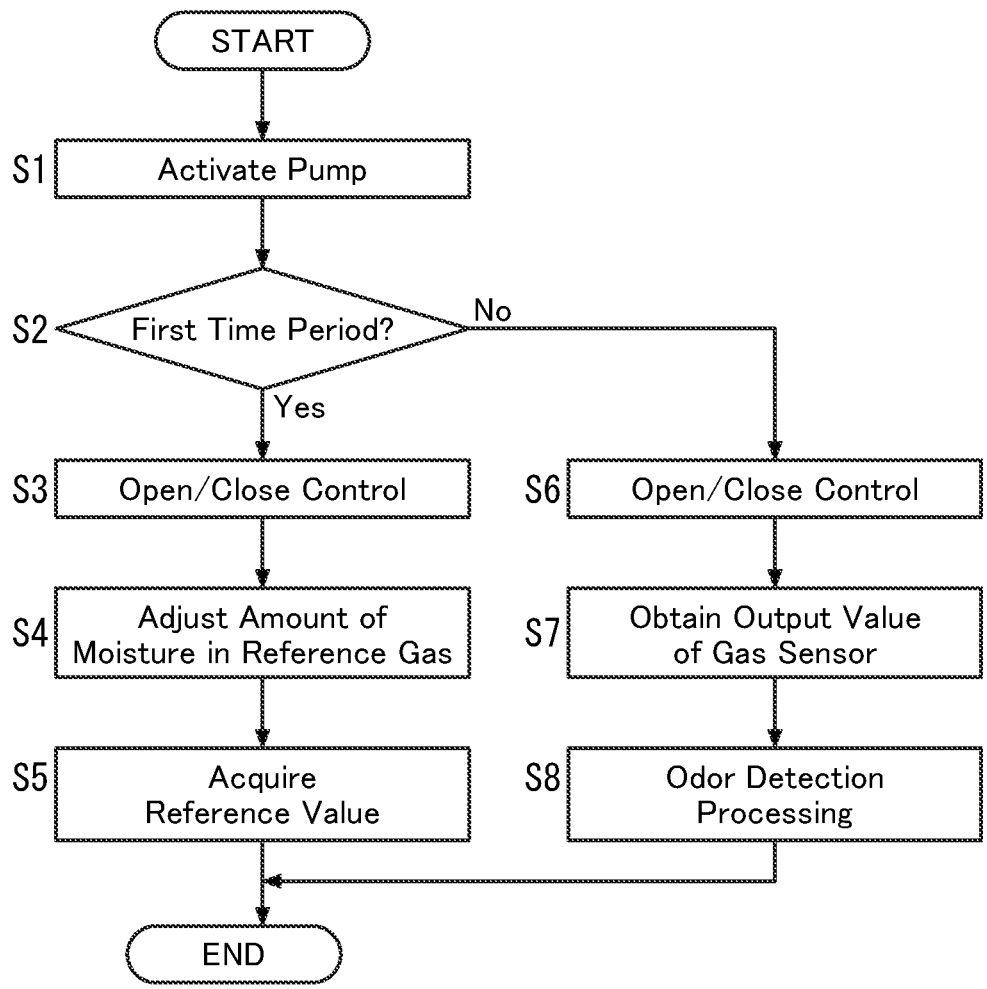
FIG. 2 is a flowchart for explaining detection operation of the gas detection system.

In the gas detection system 1 according to the sixth variation, the controller 51 in the second time period controls the two-way electromagnetic valve 73 to be switched to the close state, controls the three-way electromagnetic valve 75 such that the first input port P11 is switched to the open state and the second input port P12 is switched to the close state, and controls the three-way electromagnetic valve 78 such that the first output port P21 is switched to the close state and the second output port P22 is switched to the open state (refer to Step S6 in FIG. 2). Accordingly, the sample gas supply passage R1 is set such that the sample gas G1 introduced from the first intake port P1 flows through the piping 61a, the particle filter 71, the piping 61b, the three-way electromagnetic valve 75, the piping 63a, the second filter 40, the piping 63b, the check valve 74 and the piping 63c in that order and is introduced to the sensor chamber 100. The first sample gas discharge passage R4A (the second discharge passage R4) is set such that the sample gas G1 introduced to the sensor chamber 100 is discharged from the sensor chamber 100, flows through the piping 64a, the electromagnetic proportional control valve 76, the piping 64b, the check valve 77, the piping 64c, the three-way electromagnetic valve 78, the piping 66, the piping 65d, the air pump 90 and the piping 67 in that order, and is discharged from the gas outlet port P3. In this state when the controller 51 starts the operation of the air pump 90, the sample gas G1 sucked from the first intake port P1 flows through the second sample gas supply passage R1B and is introduced to the sensor chamber 100, and then flows through the first sample gas discharge passage R4A (the second discharge passage R4) and is discharged from the gas outlet port P3. In the sixth variation, the sample gas supply passage R1 is a flow path in which gas passes through only the second filter 40 without passing through the first filter 30, and this flow path is also referred to as a "second sample gas supply passage R1B." In other words, the gas detection system 1 according to the sixth variation includes the second sample gas supply passage R1B that is disposed to supply the sample gas G1 to the sensor chamber 100 not through the first filter 30 but through the second filter 40. The gas detection system 1 according to the sixth variation performs, when supplying the sample gas G1 to the sensor chamber 100, a second sample gas supply processing that includes supplying the sample gas G1 to the sensor chamber 100 through the sample gas supply passage R1B, which passes not through the first filter 30 but through the second filter 40.

In the gas detection system 1, the moisture in the sample gas G1 is reduced by causing the sample gas G1 to pass through the second filter 40, which can reduce a chance that the output value of the gas sensor 11 is affected by the moisture in the sample gas G1, and can therefore reduce a measurement error that may occur due to the moisture.

Figure 10:
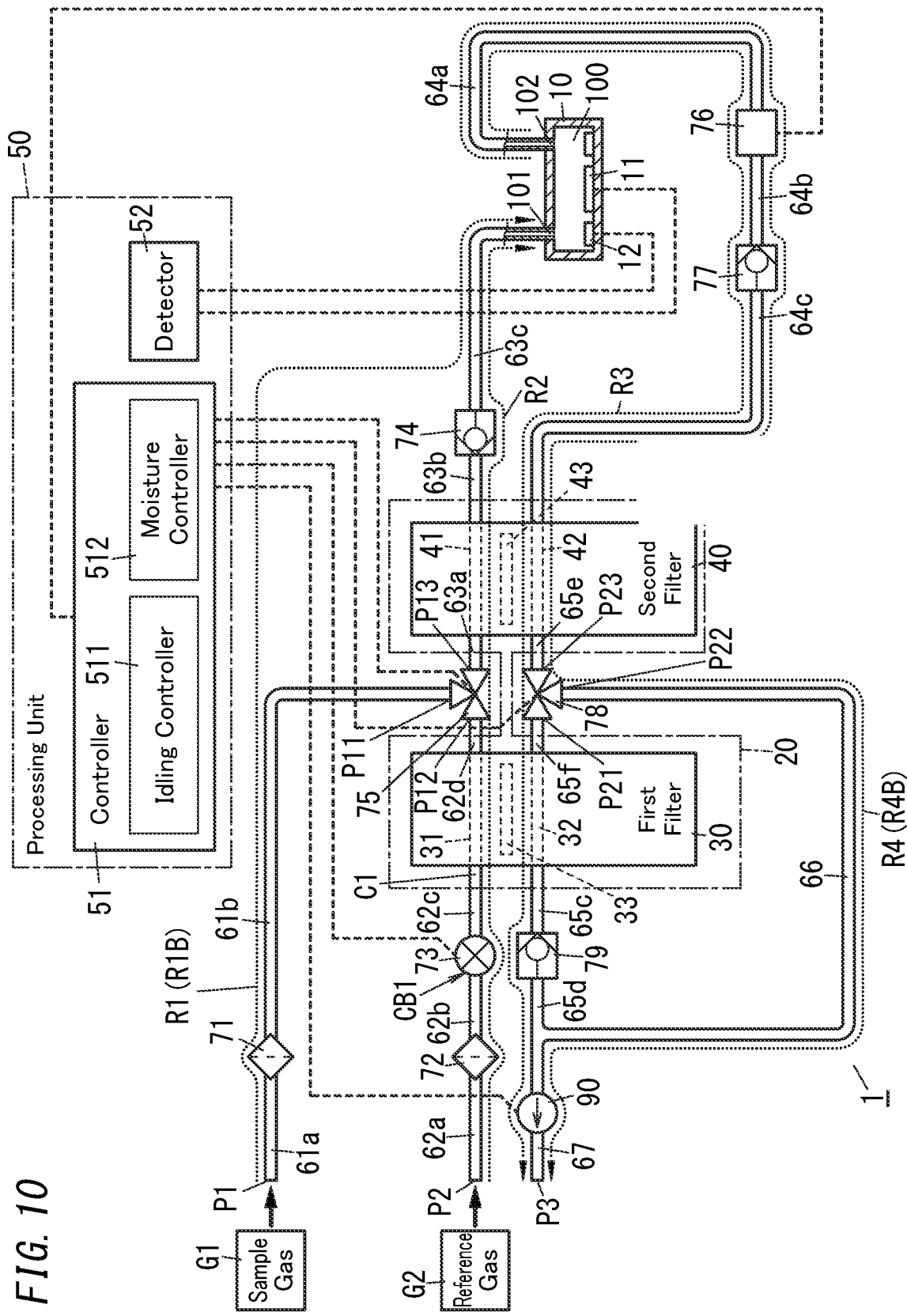
FIG. 10 is a schematic system configuration diagram showing a seventh variation of the gas detection system.

In the gas detection system 1 according to the sixth variation, the second discharge passage R4 for discharging the sample gas G1 is provided not to pass through the filter unit 20. However, this is only an example and should not be construed as limiting. As a seventh variation illustrated in FIG. 10, the second discharge passage R4 may be provided so as to pass through only the second filter 40 for moisture, of the filter unit 20.

In the gas detection system 1 according to the seventh variation, the second passage 42 of the second filter 40 is connected to the input port P23 of the three-way electromagnetic valve 78 with the piping 65e, and the first output port P21 of the three-way electromagnetic valve 78 is connected to the second passage 32 of the first filter 30 with the piping 65f. The second output port P22 of the three-way electromagnetic valve 78 is connected to the piping 65d with the piping 66. The output port of the check valve 77 is connected to the second passage 42 of the second filter 40 with the piping 64c.

The operation of the gas detection system 1 according to the seventh variation is similar to the operation of the gas detection system 1 according to the sixth variation described above, except for the processing (refer to Step S6 in FIG. 2) supplying the sample gas G1 to the sensor chamber 100 through the second sample gas supply passage R1B and then discharging it from the gas outlet port P3 to the outside through the second discharge passage R4. Since the reference gas supply processing (refer to Step S3 in FIG. 2) supplying the reference gas G2 to the sensor chamber 100 in the gas detection system 1 is similar to that in the gas detection system 1 of the foregoing embodiment, the explanation thereof will be omitted.

In the gas detection system 1 according to the seventh variation, the controller 51 in the second time period controls the two-way electromagnetic valve 73 to be switched to the close state, controls the three-way electromagnetic valve 75 such that the first input port P11 is switched to the open state and the second input port P12 is switched to the close state, and controls the three-way electromagnetic valve 78 such that the first output port P21 is switched to the close state and the second output port P22 is switched to the open state (refer to Step S6 in FIG. 2). Accordingly, the second sample gas supply passage R1B is set such that the sample gas G1 introduced from the first intake port P1 flows through the piping 61a, the particle filter 71, the piping 61b, the three-way electromagnetic valve 75, the piping 63a, the second filter 40, the piping 63b, the check valve 74 and the piping 63c in that order and is introduced to the sensor chamber 100.

The second discharge passage R4 is set such that the sample gas G1 introduced to the sensor chamber 100 is discharged from the sensor chamber 100, flows through the piping 64a, the electromagnetic proportional control valve 76, the piping 64b, the check valve 77, the piping 64c, the second filter 40, the piping 65e, the three-way electromagnetic valve 78, the piping 66, the piping 65d, the air pump 90 and the piping 67 in that order, and is discharged from the gas outlet port P3. In this state when the controller 51 starts the operation of the air pump 90, the sample gas G1 sucked from the first intake port P1 flows through the sample gas supply passage R1 and is supplied to the sensor chamber 100. Then, the sample gas G1 supplied to the sensor chamber 100 flows through the second discharge passage R4 and is discharged from the gas outlet port P3 to the outside.

In the gas detection system 1 according to the seventh variation, the second discharge passage R4 as the sample gas discharge passage is a flow path in which gas in the sensor chamber 100 is caused to pass through the second filter 40 and then discharged from the gas outlet port P3 to the outside not through the first filter 30, and this flow path is also referred to as a "second sample gas supply passage R1B."

As described above, the gas detection system 1 according to the seventh variation causes the sample gas G1 introduced to the sensor chamber 100 to flow through the second sample gas discharge passage R4B and discharges the sample gas G1 to the outside. The second sample gas discharge passage R4B is disposed to connect the sensor chamber 100 and the gas outlet port P3 for discharging at least the sample gas G1. The second sample gas discharge passage R4B is provided to cause the sample gas G1, discharged from the sensor chamber 100, to pass through the second filter 40, and then discharge the sample gas G1 from the gas outlet port P3 without passing through the first filter 30.

Thus, the sample gas G1 introduced from the first intake port P1 passes through the first passage 41 of the second filter 40 and is supplied to the sensor chamber 100, and then is discharged from the sensor chamber 100, passes through the second passage 42 of the second filter 40, and is discharged from the gas outlet port P3 to the outside.

Each of the second sample gas supply passage R1B and the second sample gas discharge passage R4B is disposed to pass through the second filter 40, and the moisture in the sample gas G1 can be therefore reduced, which can reduce a chance that the output value of the gas sensor 11 is affected by the moisture in the sample gas G1 and can therefore reduce the measurement error that may occur due to the moisture. In other words, since the moisture in the sample gas G1 is reduced by the second filter 40 and the VOC and the moisture in the reference gas G2 are reduced by the first filter 30 and the second filter 40, the output value of the gas sensor 11 becomes a value corresponding to the VOC in the sample gas G1 in a state where the sample gas G1 is supplied to the sensor chamber 100. Accordingly, the gas detection system 1 can detect the VOC as the detection target molecules at higher accuracy.

In the foregoing embodiment, the electromagnetic proportional control valve 76 as the variable orifice is disposed on the upstream side of the three-way electromagnetic valve 78 (on the side of the housing 10). However, this is only an example and should not be construed as limiting. Instead of the electromagnetic proportional control valve 76, a speed control valve may be disposed, which controls a flow rate of gas to be adjusted to a prescribed value. If the speed control valve is disposed instead of the electromagnetic proportional control valve 76, the gas detection system 1 can change a flow rate of gas on the downstream side of the speed control valve without changing a flow rate of gas flowing through the sensor chamber 100. Therefore, the output value of the gas sensor 11 is stabilized, which can realize stable measurement.

In the foregoing embodiment, the moisture controller 512 changes the flow rate of the reference gas G2 based on the measuring result relating to the amount of moisture in the reference gas G2 to adjust the amount of moisture in the reference gas G2 passing through the filter unit 20. However, this is only an example and should not be construed as limiting. The moisture controller 512 may change a measuring condition other than the flow rate of the reference gas G2. For example, the moisture controller 512 may change a temperature of the reference gas G2 passing through the filter unit 20 with a heater or the like based on the measuring result relating to the amount of moisture in the reference gas G2 to adjust the amount of moisture in the reference gas G2 passing through the filter unit 20.

In the foregoing embodiment, the controller 51 in the first time period may control the flow rate of the reference gas G2 passing through the filter unit 20 based on the output value of the gas sensor 11, which can supply the reference gas G2 including almost no detection target molecules to the gas sensor 11. Accordingly, the gas detection system 1 can obtain, in the first time period, the reference value in the state of being hardly affected by the detection target molecules, which can improve the accuracy in the measurement of the detection target molecules in the second time period.

In the foregoing embodiment, the sensor chamber 100 may be provided with an absorption unit including an aggregate of nanowires. The gas detection system 1 concentrates gas introduced to the sensor chamber 100 by causing the absorption unit to absorb the gas, and supplies the gas desorbed from the absorption unit to the gas sensor 11, which can improve the detection sensitivity in gas.

In the foregoing embodiment, the first time period for introducing the reference gas G2 to the sensor chamber 100 is temporally separated from the second time period for introducing the sample gas G1 to the sensor chamber 100. However, this is only an example and should not be construed as limiting. An area where the gas detection system 1 collects the sample gas G1 may be spatially separated from an area where the gas detection system 1 collects the reference gas G2.

In the foregoing embodiment, the first filter 30 for VOC and the second filter 40 for moisture are connected in series to each other. However, this is only an example and should not be construed as limiting. If the separation membrane 43 of the second filter 40 is made of a material that is hardly deteriorated by the VOC, the first filter 30 and the second filter 40 may be disposed in parallel to each other.

In the foregoing embodiment, the filter unit 20 includes the first filter 30 for VOC and the second filter 40 for moisture. However, this is only an example and should not be construed as limiting. The filter unit 20 may include only a single filter that has a separation membrane including hollow fibers, configured to reduce both of the VOC and the moisture.

(Recapitulation)

As can be seen from the foregoing description, a gas detection system (1) according to a first aspect includes a reference gas inlet port (P2), a gas sensor (11), and a filter unit (20). A reference gas (G2) is introduced from the reference gas inlet port (P2). The reference gas (G2) is used as a reference to concentration of detection target molecules in a sample gas (G1). The gas sensor (11) is configured to detect the detection target molecules. The filter unit (20) is disposed at a reference gas supply passage (R2). The reference gas supply passage (R2) connects the reference gas inlet port (P2) and a sensor chamber (100) in which the gas sensor (11) is housed. The filter unit (20) includes at least a first filter (30) and a second filter (40). The first filter (30) is configured to reduce the detection target molecules in the reference gas (G2). The second filter (40) is configured to reduce moisture in the reference gas (G2). Each of the first filter (30) and the second filter (40) has a separation membrane (33, 43) including hollow fibers.

According to this aspect, the gas detection system (1) can realize suppressing deterioration of the filter unit (20).

A gas detection system (1) according to a second aspect, which may be implemented in conjunction with the first aspect, further includes a shutoff unit (CB1). The shutoff unit (CB1) is configured to shut off outside air toward the filter unit (20) in a stop state where detection operation of the gas sensor (11) is stopped.

According to this aspect, the gas detection system (1) can realize suppressing deterioration of the filter unit (20).

In a gas detection system (1) according to a third aspect, which may be implemented in conjunction with the second aspect, the shutoff unit (CB1) includes a check valve (74).

According to this aspect, the gas detection system (1) can realize suppressing deterioration of the filter unit (20).

In a gas detection system (1) according to a fourth aspect, which may be implemented in conjunction with the second or third aspect, the filter unit (20) is connected to an outside by two or more flow passages including the reference gas supply passage (R2). The shutoff unit (CB1) includes two or more shutoff elements disposed at the two or more flow passages, respectively. Each of the two or more shutoff elements is provided to shut-off a corresponding flow passage of the two or more flow passages between the filter unit (20) and the outside in the stop state.

According to this aspect, the gas detection system (1) can realize suppressing deterioration of the filter unit (20).

A gas detection system (1) according to a fifth aspect, which may be implemented in conjunction with any one of the second to fourth aspects, further includes an idling controller (511). The idling controller (511) is configured to switch the shutoff unit (CB1) to a non-shutoff state and perform idling operation to supply the reference gas (G2) to the gas sensor (11) in the stop state.

According to this aspect, the gas detection system (1) can realize suppressing deterioration of the filter unit (20).

In a gas detection system (1) according to a sixth aspect, which may be implemented in conjunction with any one of the first to fifth aspects, the first filter (30) and the second filter (40) are disposed between the reference gas inlet port (P2) and the sensor chamber (100) such that the first filter (30) is positioned between the reference gas inlet port (P2) and the second filer (40).

According to this aspect, the gas detection system (1) can realize suppressing deterioration of the filter unit (20).

A gas detection system (1) according to a seventh aspect, which may be implemented in conjunction with any one of the first to sixth aspects, further includes a moisture measuring unit (12) and a moisture controller (512). The moisture measuring unit (12) is configured to measure an amount of moisture contained in the reference gas (G2) after passing through the filter unit (20). The moisture controller (512) is configured to adjust the amount of moisture of the reference gas (G2) to be supplied to the gas sensor (11) through the filter unit (20) based on a measuring result of the moisture measuring unit (12).

According to this aspect, it is possible to provide the gas detection system (1), which can realize reducing variation in detection results relating to the sample gas.

A gas detection system (1) according to an eighth aspect, which may be implemented in conjunction with any one of the first to seventh aspects, further includes a first sample gas supply passage (R1A). The first sample gas supply passage (R1A) is disposed to supply the sample gas (G1) to the sensor chamber (100) not through the filter unit (20).

According to this aspect, the gas detection system (1) can realize suppressing deterioration of the filter unit (20).

A gas detection system (1) according to a ninth aspect, which may be implemented in conjunction with any one of the first to seventh aspects, further includes a second sample gas supply passage (R1B). The second sample gas supply passage (R1B) is disposed to supply the sample gas (G1) to the sensor chamber (100) not through the first filter (30) but through the second filter (40).

According to this aspect, the gas detection system (1) can realize suppressing deterioration in detection accuracy relating to the detection target molecules.

A control method for a gas detection system (1), according to a tenth aspect, includes a reference gas supply processing. The reference gas supply processing includes supplying a reference gas (G2) to a sensor chamber (100), in which a gas sensor (11) is housed, through a filter unit (20). The reference gas (G2) is used as a reference to concentration of detection target molecules in a sample gas (G1). The filter unit (20) includes at least a first filter (30) and a second filter (40). The first filter (30) is configured to reduce the detection target molecules in the reference gas (G2). The second filter (40) is configured to reduce moisture in the reference gas (G2). Each of the first filter (30) and the second filter (40) has a separation membrane (33, 43) including hollow fibers.

According to this aspect, the control method can realize suppressing deterioration of the filter unit (20).

A control method for a gas detection system (1), according to an eleventh aspect, which may be implemented in conjunction with the tenth aspect, further include a shutoff processing. The shutoff processing includes shutting off outside air toward the filter unit (20) in a stop state where detection operation of the gas sensor (11) is stopped.

According to this aspect, the control method can realize suppressing deterioration of the filter unit (20).

A control method for a gas detection system (1), according to a twelfth aspect, which may be implemented in conjunction with the tenth or eleventh aspect, further includes a moisture measuring processing and a moisture adjustment processing. The moisture measuring processing includes measuring an amount of moisture contained in the reference gas (G2) after passing through the filter unit (20). The third processing includes adjusting the amount of moisture of the reference gas (G2) to be supplied to the gas sensor (11) through the filter unit (20) based on a measuring result relating to the amount of moisture.

According to this aspect, it is possible to provide the control method for the gas detection system (1), which can realize reducing variation in detection results relating to the sample gas.

In a control method for a gas detection system (1), according to a thirteenth aspect, which may be implemented in conjunction with the twelfth aspect, the moisture measuring processing includes measuring the amount of moisture contained in the reference gas (G2), based on a measuring result relating to a temperature and a humidity of the reference gas (G2), in a reference gas supply passage (R2) in which the reference gas (G2) flows after passing through the filter unit (20).

According to this aspect, it is possible to provide the control method for the gas detection system (1), which can realize reducing variation in detection results relating to the sample gas.

In a control method for a gas detection system (1), according to a fourteenth aspect, which may be implemented in conjunction with the twelfth or thirteenth aspect, the moisture adjustment processing includes adjusting a pressure difference of the separation membrane (43) of the second filter (40).

According to this aspect, it is possible to provide the control method for the gas detection system (1), which can realize reducing variation in detection results relating to the sample gas.

In a control method for a gas detection system (1), according to a fifteenth aspect, which may be implemented in conjunction with any one of the eleventh to fourteenth aspects, the reference gas supply processing includes supplying the reference gas (G2) to the sensor chamber (100) by causing the reference gas (G2) to pass through the first filter (30) and then pass through the second filter (40).

According to this aspect, it is possible to provide the control method for the gas detection system (1), which can realize reducing variation in detection results relating to the sample gas.

In a control method for a gas detection system (1), according to a sixteenth aspect, which may be implemented in conjunction with any one of the eleventh to fifteenth aspects, further includes a first sample gas supply processing. The first sample gas supply processing includes supplying the sample gas (G1) to the sensor chamber (100) by causing the sample gas (G1) to pass through a first sample gas supply passage (R1A) disposed not to pass through the filter unit (20).

According to this aspect, the control method can realize suppressing deterioration of the filter unit (20).

A control method for a gas detection system (1), according to a seventeenth aspect, which may be implemented in conjunction with the sixteenth aspect, further includes discharging the sample gas (G1), introduced into the sensor chamber (100), through a first sample gas discharge passage (R4A). The first sample gas discharge passage (R4A) is disposed to connect the sensor chamber (100) and a gas outlet port (P3) for discharging at least the sample gas (G1) without passing through the filter unit (20).

According to this aspect, the control method can realize suppressing deterioration of the filter unit (20).

A gas supply method for a gas detection system (1), according to an eighteenth aspect, which may be implemented in conjunction with any one of the eleventh to fifteenth aspects, further includes a second sample gas supply processing. The second sample gas supply processing includes supplying the sample gas (G1) to the sensor chamber (100) through a sample gas supply passage (R1B), which passes not through the first filter (30) but through the second filter (40).

According to this aspect, the method can realize suppressing deterioration in detection accuracy relating to the detection target molecules.

A gas supply method for a gas detection system (1), according to a nineteenth aspect, which may be implemented in conjunction with the eighteenth aspect, further includes discharging the sample gas (G1), introduced into the sensor chamber (100), through a second sample gas discharge passage (R4B). The second sample gas discharge passage (R4B) is disposed to connect the sensor chamber (100) and a gas outlet port (P3) for discharging at least the sample gas (G1). The control method further includes causing the sample gas (G1), discharged from the sensor chamber (100), to pass through the second filter (40), and then discharging the sample gas (G1) from the gas outlet port (P3) without passing through the first filter (30).

According to this aspect, the method can realize suppressing deterioration in detection accuracy relating to the detection target molecules.

A gas supply method for a gas detection system (1), according to a twentieth aspect, which may be implemented in conjunction with any one of the tenth to nineteenth aspects, further includes causing the reference gas (G2) supplied to the sensor chamber (100) to pass through the second filter (40) and the first filter (30) in that order, and then discharging the reference gas (G2).

According to this aspect, the method can realize suppressing deterioration in detection accuracy relating to the detection target molecules.

In a gas detection system (1) according to a twenty-first aspect, which may be implemented in conjunction with the first aspect, the shutoff unit (CB1) includes an electromagnetic selector valve (73, 75, 78) configured to switch to either an open state or a close state by electromagnetic force.

According to this aspect, the gas detection system (1) can realize suppressing deterioration of the filter unit (20).

The configurations of the gas detection system (1) are not limited to the above aspects. Various configurations (including variations) of the gas detection system (1) according to the embodiment described above may be implemented as a control method of the gas detection system (1), a (computer) program, or a non-transitory storage medium that stores the program.

Note that the constituent elements according to the second to ninth, and twenty-first aspects are not essential constituent elements for the gas detection system (1) but may be omitted as appropriate. Also, the constituent elements according to the eleventh to twentieth aspects are not essential constituent elements for the control method for the gas detection system (1) but may be omitted as appropriate.

REFERENCE SIGNS LIST

1 Gas Detection System
11 Gas Sensor
12 Moisture Measuring Unit
20 Filter Unit
30 First Filter
33 Separation Membrane
40 Second Filter
43 Separation Membrane
51 Controller
73 Two-way Electromagnetic Valve (Electromagnetic Selector Valve)
74 Check Valve
75, 78 Three-way Electromagnetic Valve (Electromagnetic Selector Valve)
100 Sensor Chamber
511 Idling Controller
512 Moisture Controller
CB1 Shutoff Unit
G1 Sample Gas
G2 Reference Gas
P2 Reference Gas Inlet Port
P3 Gas Outlet Port
R1A First Sample Gas Supply Passage
R1B Second Sample Gas Supply Passage
R2 Reference Gas Supply Passage
R4A First Sample Gas Discharge Passage
R4B Second Sample Gas Discharge Passage

The invention claimed is:

1. A gas detection system, comprising:
a reference gas inlet port from which a reference gas is introduced, the reference gas being used as a reference to concentration of detection target molecules in a sample gas;
a gas sensor configured to detect the detection target molecules;
a sensor chamber in which the gas sensor is housed;
a filter unit disposed at a reference gas supply passage connecting the reference gas inlet port and the sensor chamber; and
a first sample gas discharge passage disposed to connect the sensor chamber and a gas outlet port for discharging at least the sample gas, wherein:
the filter unit includes at least a first filter and a second filter, the first filter being configured to reduce the detection target molecules in the reference gas, and the second filter being configured to reduce moisture in the reference gas,
each of the first filter and the second filter includes a separation membrane including hollow fibers, and
the first sample gas discharge passage passes through the filter unit.

2. The gas detection system of claim 1, further comprising a shutoff unit configured to shut off outside air toward the filter unit in a stop state where detection operation of the gas sensor is stopped.

3. The gas detection system of claim 2, wherein
the shutoff unit includes a check valve.

4. The gas detection system of claim 2, wherein
the filter unit is connected to an outside by two or more flow passages including the reference gas supply passage,
the shutoff unit includes two or more shutoff elements disposed at the two or more flow passages, respectively, and
each of the two or more shutoff elements is provided to shut-off a corresponding flow passage of the two or more flow passages between the filter unit and the outside in the stop state.

5. The gas detection system of claim 2, further comprising an idling controller configured to switch the shutoff unit to a non-shutoff state and perform idling operation to supply the reference gas to the gas sensor in the stop state.

6. The gas detection system of claim 1, wherein
the first filter and the second filter are disposed between the reference gas inlet port and the sensor chamber such that the first filter is positioned between the reference gas inlet port and the second filer.

7. The gas detection system of claim 1, further comprising:
a moisture measuring unit configured to measure an amount of moisture contained in the reference gas after passing through the filter unit; and
a moisture controller configured to adjust the amount of moisture of the reference gas to be supplied to the gas sensor through the filter unit based on a measuring result of the moisture measuring unit.

8. The gas detection system of claim 1, further comprising a first sample gas supply passage disposed to supply the sample gas to the sensor chamber not through the filter unit.

9. The gas detection system of claim 1, further comprising a second sample gas supply passage disposed to supply the sample gas to the sensor chamber not through the first filter but through the second filter.

10. A control method for a gas detection system, the control method comprising:
a reference gas supply processing including supplying a reference gas to a sensor chamber, in which a gas sensor is housed, through a filter unit including at least a first filter and a second filter;
a moisture measuring processing including measuring an amount of moisture contained in the reference gas after passing through the filter unit; and
a moisture adjustment processing including adjusting the amount of moisture of the reference gas to be supplied to the gas sensor through the filter unit based on a measuring result relating to the amount of moisture, wherein:
the reference gas is used as a reference to concentration of detection target molecules in a sample gas,
the first filter is configured to reduce the detection target molecules in the reference gas, and the second filter being configured to reduce moisture in the reference gas, and
each of the first filter and the second filter includes a separation membrane including hollow fibers.

11. The control method of claim 10, further comprising a shutoff processing including shutting off outside air toward the filter unit in a stop state where detection operation of the gas sensor is stopped.

12. The control method of claim 11, wherein
the reference gas supply processing includes supplying the reference gas to the sensor chamber by causing the reference gas to pass through the first filter and then pass through the second filter.

13. The control method of claim 11, further comprising a first sample gas supply processing including supplying the sample gas to the sensor chamber by causing the sample gas to pass through a first sample gas supply passage disposed not to pass through the filter unit.

14. The control method of claim 13, further comprising discharging the sample gas, introduced into the sensor chamber, through a first sample gas discharge passage, wherein
the first sample gas discharge passage is disposed to connect the sensor chamber and a gas outlet port for discharging at least the sample gas without passing through the filter unit.

15. The control method of claim 11, further comprising a second sample gas supply processing including supplying the sample gas to the sensor chamber through a sample gas supply passage, which passes not through the first filter but through the second filter.

16. The control method of claim 15, further comprising discharging the sample gas, introduced into the sensor chamber, through a second sample gas discharge passage, wherein
the second sample gas discharge passage is disposed to connect the sensor chamber and a gas outlet port for discharging at least the sample gas, and
the control method further comprising causing the sample gas, discharged from the sensor chamber, to pass through the second filter, and then discharging the sample gas from the gas outlet port without passing through the first filter.

17. The control method of claim 10, wherein
the moisture measuring processing includes measuring the amount of moisture contained in the reference gas, based on a measuring result relating to a temperature and a humidity of the reference gas, in a reference gas supply passage in which the reference gas flows after passing through the filter unit.

18. The control method of claim 10, wherein
the moisture adjustment processing includes adjusting a pressure difference of the separation membrane of the second filter.

19. The control method of claim 10, further comprising causing the reference gas supplied to the sensor chamber to pass through the second filter and the first filter in that order, and then discharging the reference gas.

* * * * *